US009617304B2

(12) United States Patent
Park et al.

(10) Patent No.: US 9,617,304 B2
(45) Date of Patent: Apr. 11, 2017

(54) PHARMACEUTICAL COMPOSITION CONTAINING AN ENDOCYTIC MOTIF AND PROTEIN TRANSDUCTION DOMAINS FOR PREVENTING OR TREATING CANCER

(75) Inventors: Young Woo Park, Daejeon (KR); Ki Won Jo, Daejeon (KR); Kyu Won Cho, Daejeon (KR); Ji Hyun Park, Daejeon (KR); Soon Sil Hyun, Daejeon (KR); Yun Jung Park, Daejeon (KR)

(73) Assignee: Korea Research Institute Of Bioscience And Biotechnology, Daejeon (KR)

( * ) Notice: Subject to any disclaimer, the term of this patent is extended or adjusted under 35 U.S.C. 154(b) by 56 days.

(21) Appl. No.: 14/002,600

(22) PCT Filed: Mar. 2, 2012

(86) PCT No.: PCT/KR2012/001593
§ 371 (c)(1),
(2), (4) Date: Nov. 12, 2013

(87) PCT Pub. No.: WO2012/118353
PCT Pub. Date: Sep. 7, 2012

(65) Prior Publication Data
US 2014/0066375 A1  Mar. 6, 2014

(30) Foreign Application Priority Data
Mar. 2, 2011  (KR) ........................ 10-2011-0018628

(51) Int. Cl.
*C07K 7/08* (2006.01)
*C07K 14/00* (2006.01)
*C07K 14/475* (2006.01)
*A61K 38/00* (2006.01)

(52) U.S. Cl.
CPC .............. *C07K 7/08* (2013.01); *C07K 14/00* (2013.01); *C07K 14/4753* (2013.01); *A61K 38/00* (2013.01); *C07K 2319/10* (2013.01)

(58) Field of Classification Search
None
See application file for complete search history.

(56) References Cited

U.S. PATENT DOCUMENTS

| | | | | |
|---|---|---|---|---|
| 5,595,756 A | * | 1/1997 | Bally et al. | 424/450 |
| 7,432,044 B2 | | 10/2008 | Kirchhofer et al. | |
| 2008/0261965 A1 | * | 10/2008 | Flynn et al. | 514/230.5 |
| 2008/0293634 A1 | | 11/2008 | Harding et al. | |

FOREIGN PATENT DOCUMENTS

WO  2009-103555 A2  8/2009
WO  2009-140549 A1  11/2009

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Bonovas et al (Anticancer Research. 28: 1857-1866 (2008)).*
Auerbach et al (Cancer and Metastasis Reviews, 2000, 19: 167-172).*
Gura T (Science, 1997, 278(5340): 1041-1042, encloses 1-5).*
Jain RK (Scientific American, Jul. 1994,58-65).*
Sporn et al, "Chemoprevention of Cancer," Carcinogenesis, vol. 21 (2000), 525-530.*
Ma (Modern Drug Discovery 2004, 7(6)).*
Choi et al (Adv Drug Deliv Rev. Dec. 15, 2014;79-80:222-37).*
Comogolio et al., "Drug development of MET inhibitors: targeting oncogene addiction and expedience," Nature 7: 504-516, Jun. 2008.
Craven et al., "Synaptic Targeting of the Postsynaptic Density Protein PSD-95 Mediated by a Tyrosine-based Trafficking Signal," The Journal of Biological Chemistry 275: 20045-20051, 2000.
DeRossi et al., "Cell Internalization of the Third Helix of the Antennapedia Homeodomain is Receptor-independent," The Journal of Biological Chemistry 271: 18188-18193, 1996.
Elliott et al., "Intercellular Trafficking and Protein Delivery by a Herpesvirus Structural Protein," Cell 88: 223-233, Jan. 24, 1997.
Jin et al., "MetMAb, the One-Armed 5D5 Anti-c-Met Antibody, Inhibits Orthotopic Pancreatic Tumor Growth and Improves Survival," Cancer Research 68: 4360-4368, 2008.
Kamei et al., "Coendocytosis of cadherin and c-Met coupled to disruption of cell-cell adhesion in MDCK cells—regulation by Rho, Rac and Rab small G proteins," Oncogene 18: 6776-6784, 1999.
Kermorgant et al., "PKC controls HGF-dependent c-Met traffic, signalling and cell migration," The EMBO Journal 23: 3721-3734, 2004.
Kermorgant et al., "Receptor trafficking controls weak signal delivery: a strategy used by c-Met for STAT3 nuclear accumulation," The Journal of Cell Biology 182(5): 855-863, 2008.
Kirchhausen et al., "Linking cargo to vesicle formation: receptor tail interactions with coat proteins," Current Opinion in Cell Biology 9: 488-495, 1997.
Li et al., "The Listeria Protein Internalin B Mimics Hepatocyte Growth Factor-Induced Receptor Trafficking," Traffic 6: 459-473, 2005.
Li et al., "Specific Grb2-mediated Interactions Regulate Clathrin-dependent Endocytosis of the cMet-tyrosine Kinase," The Journal of Biological Chemistry 282: 16764-16775, 2007.
Petrelli et al., "The endophilin-CIN85-Cbl complex mediates ligand-dependent downregulation of c-Met," Nature 416: 187-190, Mar. 14, 2002.
Polo et al., "Endocytosis Conducts the Cell Signaling Orchestra," Cell 124: 897-900, Mar. 10, 2006.
Schmidt et al., "Endocytosis of the glucose transporter GLUT8 is mediated by interaction of a dileucine motif with the beta2-adaptin subunit of the AP-2 adaptor complex," Journal of Cell Science 119(11): 2321-2331, 2006.

* cited by examiner

*Primary Examiner* — Brian J Gangle
*Assistant Examiner* — Andrea McCollum

(57) ABSTRACT

The present invention relates to a novel endocytic motif, and in particular, to a fusion polypeptide including the motif represented by an amino acid sequence of SEQ ID NO. 1 and a protein transduction domain, a pharmaceutical composition for preventing or treating cancer including the same, and a method for treating cancer including the step of administering the composition. The present invention shows the effects of suppressing metastasis, infiltration, angiogenesis, and growth of cancer by specifically inhibiting c-Met endocytosis and effectively inhibiting HGF/c-Met signaling pathway associated with metastasis and growth of various types of cancer cells. Therefore, the present invention can be applied to an anticancer agent for various types of cancer.

6 Claims, 22 Drawing Sheets

FIG. 1

```
  Human   HVNATYVNVKCVAPYPSLLSSEDNADDEVDT (SEQ ID NO: 11)
    Rat   HVNATYVNVKCVAPYPSLLPSQDNIDGEANT  (SEQ ID NO: 12)
 Gallus   HVNATYVNVKCVAPYPSLLSSQDNTDMDVDT  (SEQ ID NO: 13)
Xenopus   LFNATYVNIKCAAPYPSLLSPEGNIDFSIDT  (SEQ ID NO: 14)
```

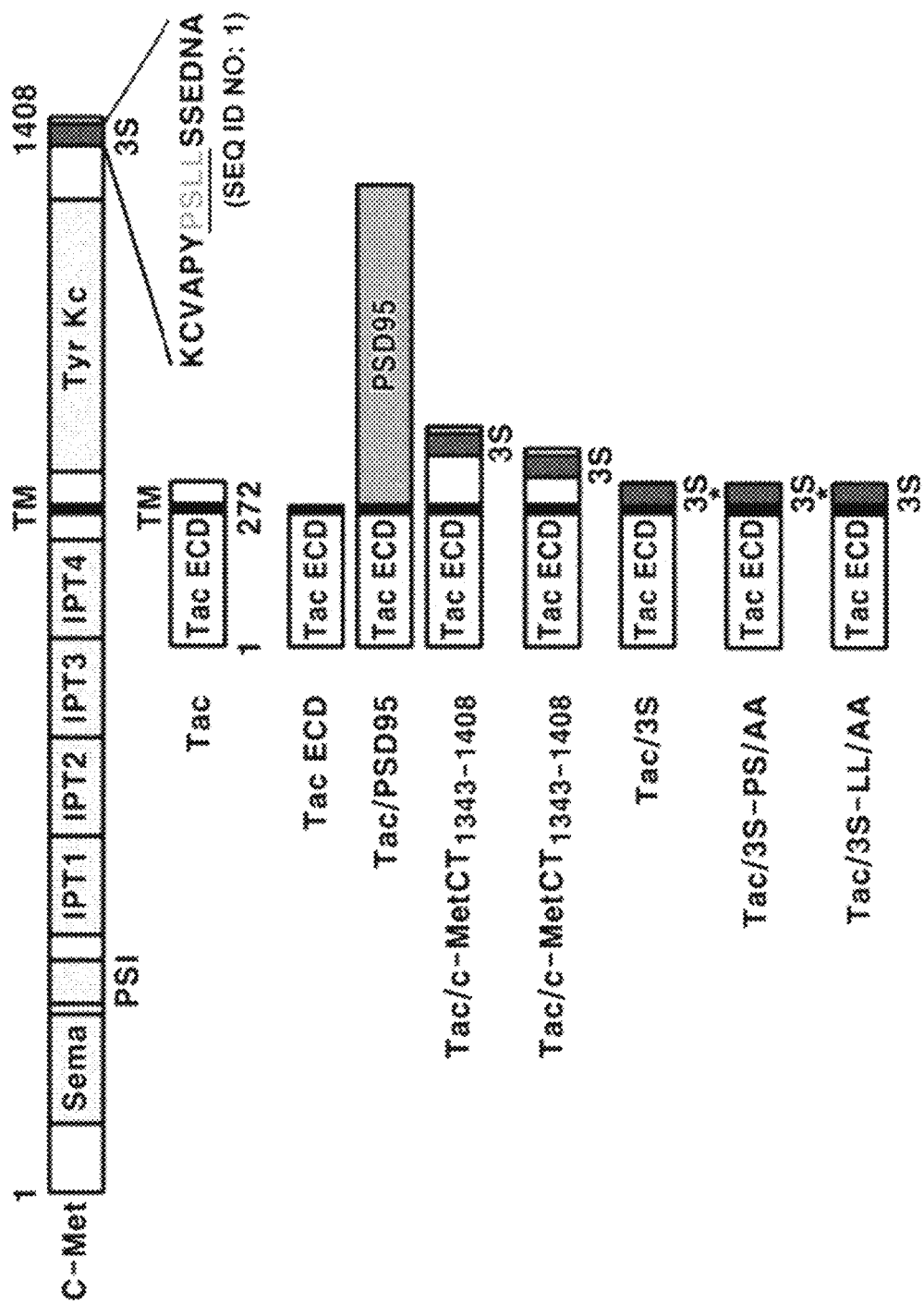

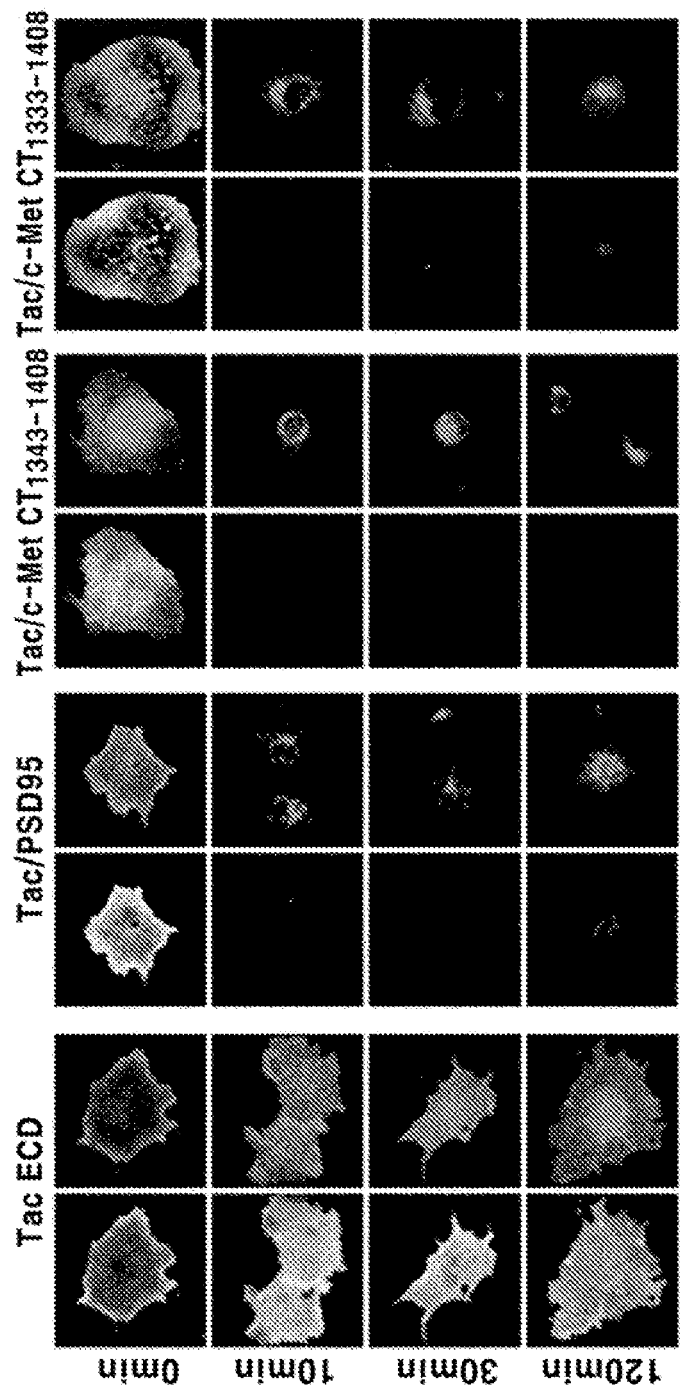

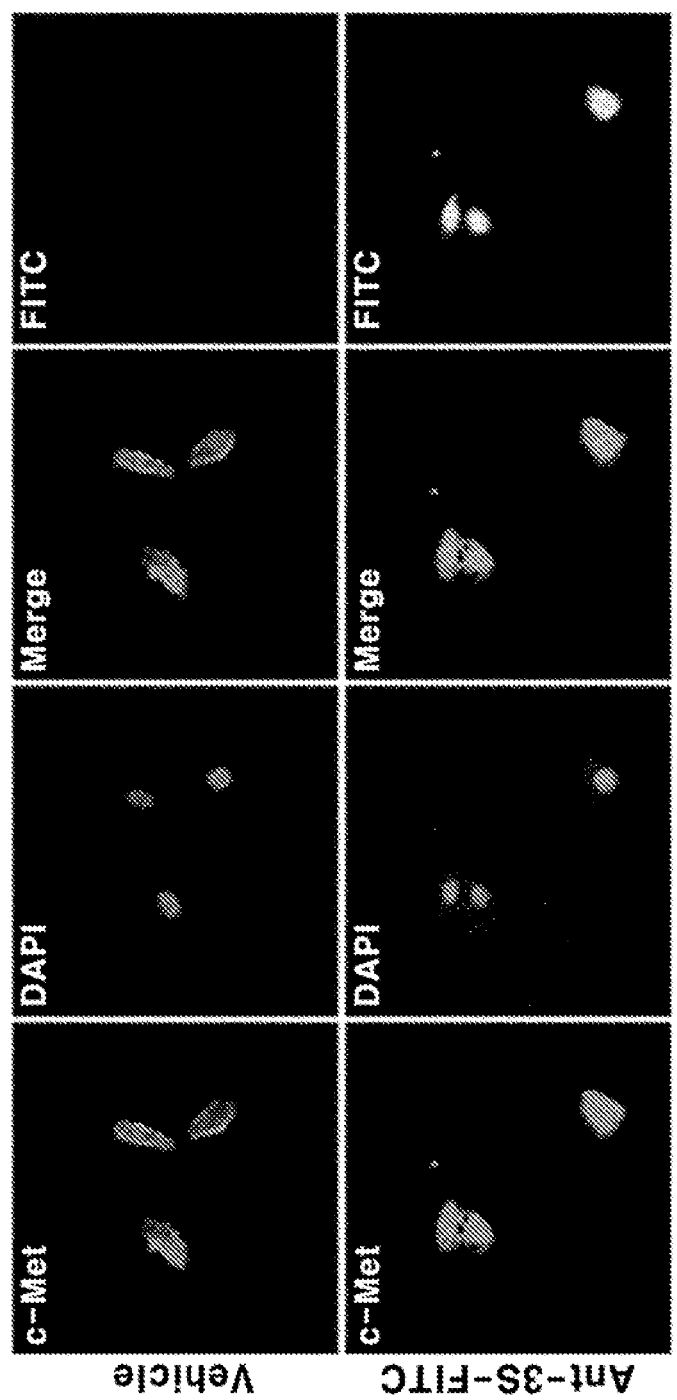

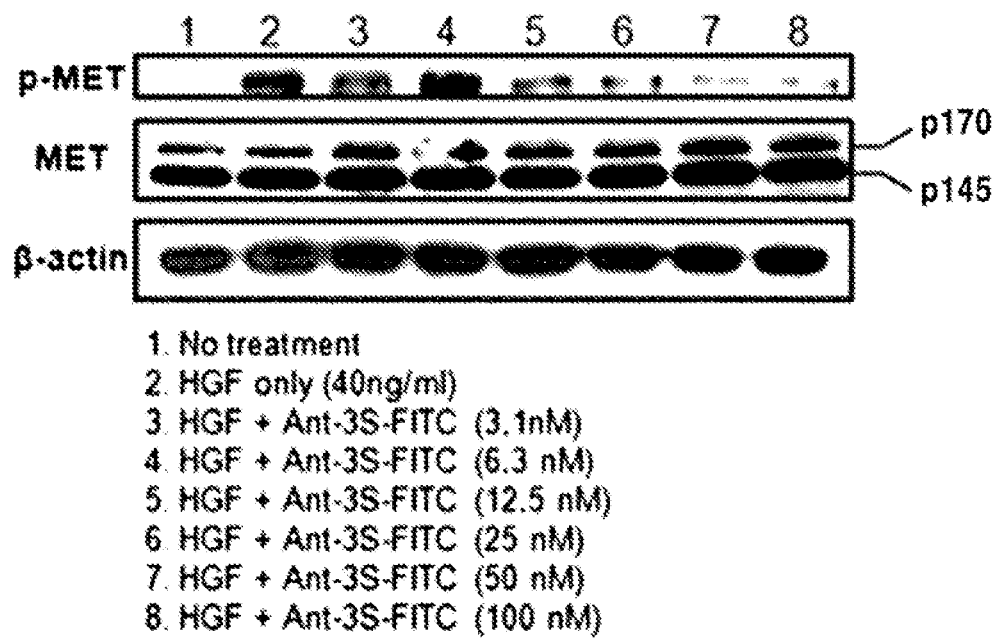

PHARMACEUTICAL COMPOSITION CONTAINING AN ENDOCYTIC MOTIF AND PROTEIN TRANSDUCTION DOMAINS FOR PREVENTING OR TREATING CANCER

CROSS-REFERENCE TO RELATED APPLICATIONS

This application is a U.S. national phase application of International PCT Patent Application No. PCT/KR2012/001593, which was filed on Mar. 2, 2012, which claims priority to Korean Patent Application No. 10-2011-0018628, filed Mar. 2, 2011. These application are incorporated herein by reference in their entireties

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_024_00US_ST25.txt. The text file is 4 KB, was created on Nov. 12, 2013, and is being submitted electronically via EFS-Web.

TECHNICAL FIELD

The present invention relates to a novel endocytic motif, and in particular, to a fusion polypeptide comprising the motif represented by an amino acid sequence of SEQ ID NO. 1 and a protein transduction domain, a pharmaceutical composition for preventing or treating cancer comprising the same, and a method for treating cancer comprising the step of administering the composition.

BACKGROUND ART

HGF (hepatocyte growth factor) is a mesenchyme-derived pleiotropic factor which has autogenic, motogenic and morphogenies activities on various different types of cells. The effects of HGF are mediated through its specific tyrosine kinase c-Met. Abnormal expression of HGF and c-Met are frequently observed in many types of cancer, and regulation of HGF/c-Met signaling pathway is known to be involved in tumor growth and metastasis.

Therefore, c-Met is an attractive target for cancer therapy owing to its significant role in the development of cancer. Overexpression of HGF/c-Met is associated with metastasis and angiogenesis of various types of epithelial cells, and from this point of view, a c-Met antagonist antibody targeting c-Met has been proposed as a potential anticancer agent (Comoglio et al., Nature Review Drug Discovery. 7:504-516, 2008). For example, it was reported that HGF-induced c-Met dimerization is negatively regulated by one-armed c-Met antibody in mouse xenograft models, resulting in suppression of tumor growth (Jin et al, Cancer Research 68(11): 4363-4368, 2008; Comoglio et al., Nature Review Drug Discovery. 7:504-516, 2003).

Meanwhile, endocytosis of receptors in response to ligands affects cellular physiology. In other words, receptor trafficking rate determines the duration and propagation of signal transduction and further regulates cell growth, motility and even the fate (Polo et al., Cell, 124(5):897-900, 2006). Therefore, applying the knowledge on molecular mechanisms of endocytosis may give way to control cellular biological processes, and also to provide the effective strategies towards the development of therapeutics.

In this regard, there have been many investigations on the underlying molecular mechanisms of c-Met. For example, it has been known that PKC (Kermorgant et al., EMBO J., 23(19):3721-34, 2004), Cbl (Petrelli et al., Nature, 416 (6877):187-93, 2002), dynamin (Dynamin; Li et al., Traffic, 6(6):459-73, 2005), Grb2 (Li et al., J Biol Chem, 282(23): 16764-75, 2007) or the like are involved in c-Met endocytosis. However, there have been no reports on the amino acid sequences of c-Met that are essential for endocytosis.

Protein transduction domain (PTD) was first identified during research on the spontaneous entry process of HIV TAT (Green et al., Cell, 55(6):1179-88, 1988). Similar studies were performed on antennapedia, *Drosophila* homeodomain transcription factor, and they revealed that 16 amino acids spanning from 43 to 58 are required (Derossi et al., J Biol Chem, 271(30):18188-93, 1996). In addition to TAT and antennapedia, VP22 proteins of HSV (Herpes simplex virus) have been also reported to have PTD function (Elliott et. al., Cell, 88:223-233, 1997).

DISCLOSURE

Technical Problem

The present inventors have researched for a new mechanism for inhibiting HGF/c-Met signaling pathway which plays an important role in cancer metastasis and growth, and identified a novel endocytic motif composed of 16 amino acids which is located in the C-terminus of c-Met. They found that internalization of this motif in cells by protein transduction domain specifically inhibits c-Met endocytosis, and furthermore inhibits migration of cancer cells, thereby completing the present invention.

Technical Solution

An object of the present invention is to provide a novel endocytic motif.

Another object of the present invention is to provide a pharmaceutical composition for preventing or treating cancer including the motif as an active ingredient.

Still another object of the present invention is to provide a fusion polypeptide represented by [N terminus-protein transduction domain-polypeptide comprising endocytic motif represented by amino acid sequence of SEQ ID NO. 1-C terminus] or [N terminus-polypeptide comprising endocytic motif represented by amino acid sequence of SEQ ID NO. 1-protein transduction domain-C terminus].

Still another object of the present invention is to provide a pharmaceutical composition for preventing or treating cancer including the fusion polypeptide.

Still another object of the present invention is to provide a method for treating cancer comprising the step of administering the composition.

Advantageous Effects

The present invention shows the effects of suppressing metastasis, infiltration, angiogenesis, and growth of cancer by specifically inhibiting c-Met endocytosis and effectively inhibiting HGF/c-Met signaling pathway associated with metastasis and growth of various types of cancer cells. Therefore, the present invention can be applied to an anticancer agent for various types of cancer.

BRIEF DESCRIPTION OF DRAWINGS

FIG. 1 shows that PSLL motif in the C-terminus of c-Met is conserved;

FIG. 2 is a schematic representation of DNA constructs of Tac chimeric proteins that were used for exploring the c-Met domain and the c-Met endocytic motif;

FIGS. 3a and 3b are fluorescence microscopic images showing endocytosis of Tac chimeric proteins depicted in FIG. 1 that were expressed in COS-7 cells;

FIG. 11 is a Western blot image showing that Ant-3S-FITC fusion polypeptide can inhibit HGF-induced autophosphorylation of c-Met and FAK;

BEST MODE

In one aspect, the present invention provides a novel endocytic motif, and preferably an endocytic motif represented by the amino acid sequence of SEQ ID NO. 1.

As used herein, the endocytic motif (hereinafter, used interchangeably with "3S polypeptide" or "3S") is a highly conserved motif composed of 16 amino acids (SEQ ID NO. 1, KCVAPYPSLLSSEDNA), which causes (induces) c-Met endocytosis and is located in the C-terminus of c-Met. This motif was first identified by the present inventors. Further, the present inventors demonstrated that dileucine in the motif is essential for c-Met endocytosis.

The endocytic motif of the present invention includes any sequences having c-Met endocytic activity without limitation, and includes an endocytic motif that is at least composed of the amino acid sequence of SEQ ID NO. 1. The sequence composed of a substitution, addition, or deletion in the amino acid of the above motif may be also included in the scope of the present invention, as long as it shows the endocytic activity. The motif may include an amino acid sequence having 75% or more, preferably 85% or more, more preferably 90% or more, much more preferably 95% or more, and most preferably 98% or more homology to the endocytic motif of SEQ ID NO. 1.

The amino acids mentioned in the present invention are abbreviated in accordance with the IUPAC-IUB nomenclature as follows.

| | |
|---|---|
| Alanine A | Arginine R |
| Asparagine N | Aspartic acid D |
| Cysteine C | Glutamic acid E |
| Glutamine Q | Glycine G |
| Histidine H | Isoleucine I |
| Leucine L | Lysine K |
| Methionine M | Phenylalanine F |
| Proline P | Serine S |
| Threonine T | Tryptophan W |
| Tyrosine Y | Valine V |

Figure 5:
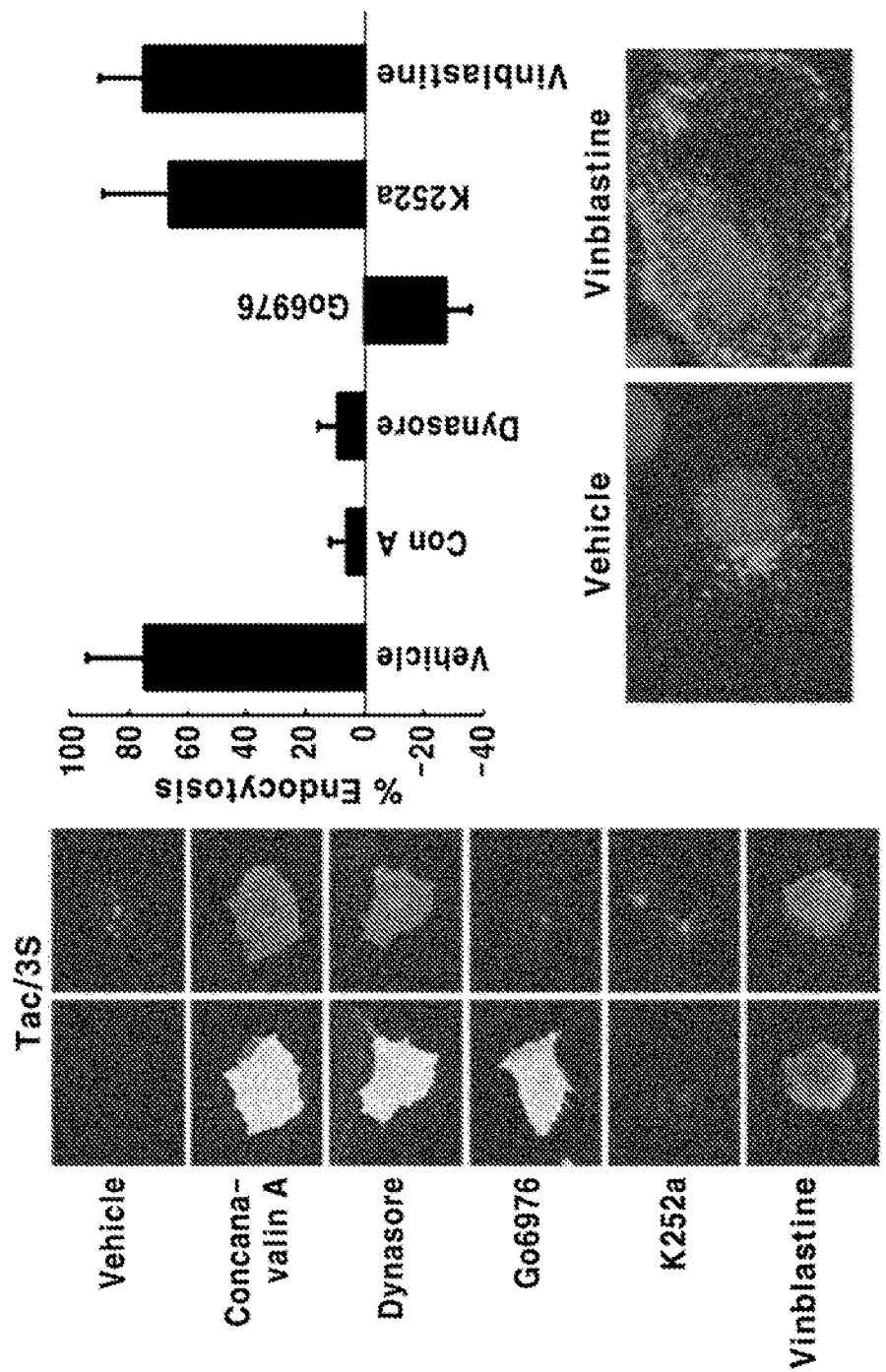
FIG. 5 is a fluorescence microscopic image showing that endocytosis was inhibited by ConA (Concannavalin A), Dynasore and Go6976, but was not inhibited by K252a and Vinblastine when Tac/3S chimeric protein was expressed in COS-7 cells to induce endocytosis.

Furthermore, to demonstrate whether the motif is internalized in cells through clathrin-mediated endocytosis like c-Met, the present inventors expressed a fusion protein (Tac/3S) of Tac and 3S polypeptide in COS-7 cells and induced endocytosis, and then treated the cells with ConA (Concannavalin A), Dynasore, Go6976, K252a and Vinblastine. As a result, when a dynamin inhibitor, Dynasore was treated, endocytosis was inhibited. Thus, it was confirmed that the motif of the present invention was internalized in cells through clathrin-mediated endocytosis like c-Met (FIG. 5).

In the present invention, the motif may have an inhibitory effect on endocytosis of one or more selected from the group consisting of c-Met, phosphorylated c-Met and c-Met bound to HGF. Further, the motif of the present invention may have an inhibitory effect on HGF-induced autophosphorylation of c-Met. Therefore, the motif of the present invention is able to block the c-Met signal transduction associated with cancer metastasis and growth by inhibiting c-Met endocytosis.

In another aspect, the present invention provides a fusion polypeptide represented by "N terminus-protein transduction domain-polypeptide comprising endocytic motif represented by amino acid sequence of SEQ ID NO. 1-C terminus" or "N terminus-polypeptide comprising endocytic motif represented by amino acid sequence of SEQ ID NO. 1-protein transduction domain-C terminus".

As used herein, the term "protein transduction domain" is a small peptide composed of basic amino acids, called CPP (cell permeable protein) or MTS (membrane translocating sequences), and refers to a protein domain that moves across the plasma membrane by itself or in conjunction with other substances, and translocates into cells without the help of a particular receptor.

In the present invention, the protein transduction domain is a means for rapid internalization of the motif of the present invention in cells, and may be, but is not limited to, any one protein transduction domain selected from the group consisting of Tat (SEQ ID NO. 2, YGRKKRRQRRR) of HIV (human immunodeficiency virus); VP22 (SEQ ID NO. 3, DAATATRGRSAASRPTERPRAPARSASAPRRPVE) of HSV (Herpes simplex virus); Antp of Drosophila (SEQ ID NO. 4, RQIKIWFQNFRMKWKK); Mph-1 (SEQ ID NO. 5, YARVRRRGPRR); Sim-2 (SEQ ID NO. 6, AKAAR-QAAR); R7 (SEQ ID NO. 7, RRRRRRR); Pep-1 (SEQ ID NO. 8, LETWWETWWTEWSQPKKKRKV); and Pep-2 (SEQ ID NO. 9, KETWFETWETEWSQPXKKRKV).

Preferably, the protein transduction domain may be Antp of Drosophila (SEQ ID NO. 4), and the fusion polypeptide may be a polypeptide that is represented by the amino acid sequence of SEQ ID NO. 10 (RQIKIMFQNRRMKWKK-KCVAPYPSLLSSEDNA).

Further, the fusion polypeptide of the present invention may further include any tag in its N-terminus and/or C-terminus for detecting the fusion polypeptide, or tracking its location in cells, and examples of the tag may include biotin signaling peptide, histidine peptide (his), hemagglutinin (HA), Flag, gold binding peptide, and fluorescent proteins such as EGFP [enhanced GFP (Green Fluorescent Protein)], blue fluorescent proteins [EBFP (Enhanced Blue Fluorescent Protein), EBFP2, Azurite, mKalamal], cyan fluorescent proteins [ECFP (Enhanced Cyan Fluorescent Protein), Cerulean, CyPet], yellow fluorescent protein derivatives [YFP (Yellow Fluorescent Protein), Citrine, Venus, YPet], BFP derivatives (Blue Fluorescent Protein derivatives), FITC (Fluorescein isothiocyanate) or the like.

Further, the fusion polypeptide of the present invention may further include a target protein. As used herein, the term "target protein" includes proteins to be introduced into cells through endocytosis by means of the fusion polypeptide of the present invention without limitation, and for example, it may be a therapeutic protein.

Further, the fusion polypeptide of the present invention may further include a compound. Preferably, the compound may be a drug including an anticancer agent or the like.

As such, the fusion polypeptide of the present invention may be used as a carrier for introducing a drug or a heterologous protein into cells. Addition of the target protein or compound to the fusion polypeptide may be performed by various methods known in the art, such as chemical, enzymatic, or genetic recombination technique, but is not limited thereto.

Figure 8:
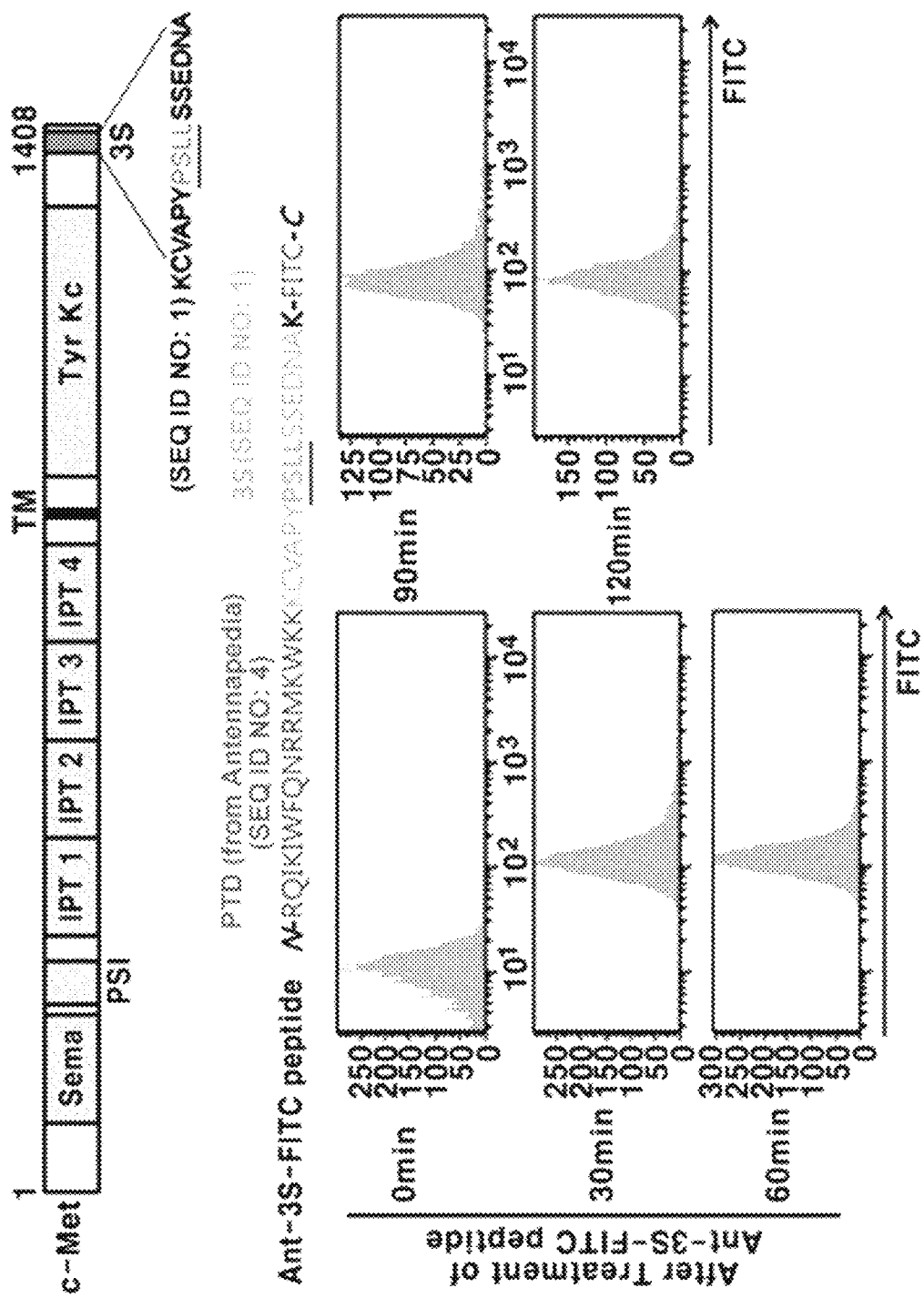
FIG. 8 is the structure and amino acid sequence (top) of Ant-3S-FITC fusion polypeptide and the FACS data (bottom) showing rapid internalization of Ant-3S-FITC fusion polypeptide in HeLa cells.

In one embodiment of the present invention, to examine rapid internalization of the fusion polypeptide (Ant-3S-FITC fusion polypeptide) represented by "N terminus-Drosophila Antp-3S polypeptide-FITC-C terminus" in cells, fluorescence intensity was measured through FACS after treatment of HeLa cells with the fusion polypeptide over time. As a result, rapid internalization of the fusion polypeptide in cells was observed (FIG. 8). This result suggests that the fusion protein of the present invention is able to introduce the compound conjugated thereto.

In the present invention, the fusion polypeptide can be rapidly internalized in cells through clathrin-mediated endocytosis, and thus inhibits endocytosis of one or more selected from the group consisting of cell surface c-Met, phosphorylated c-Met and c-Met bound to HGF.

Figure 9A:
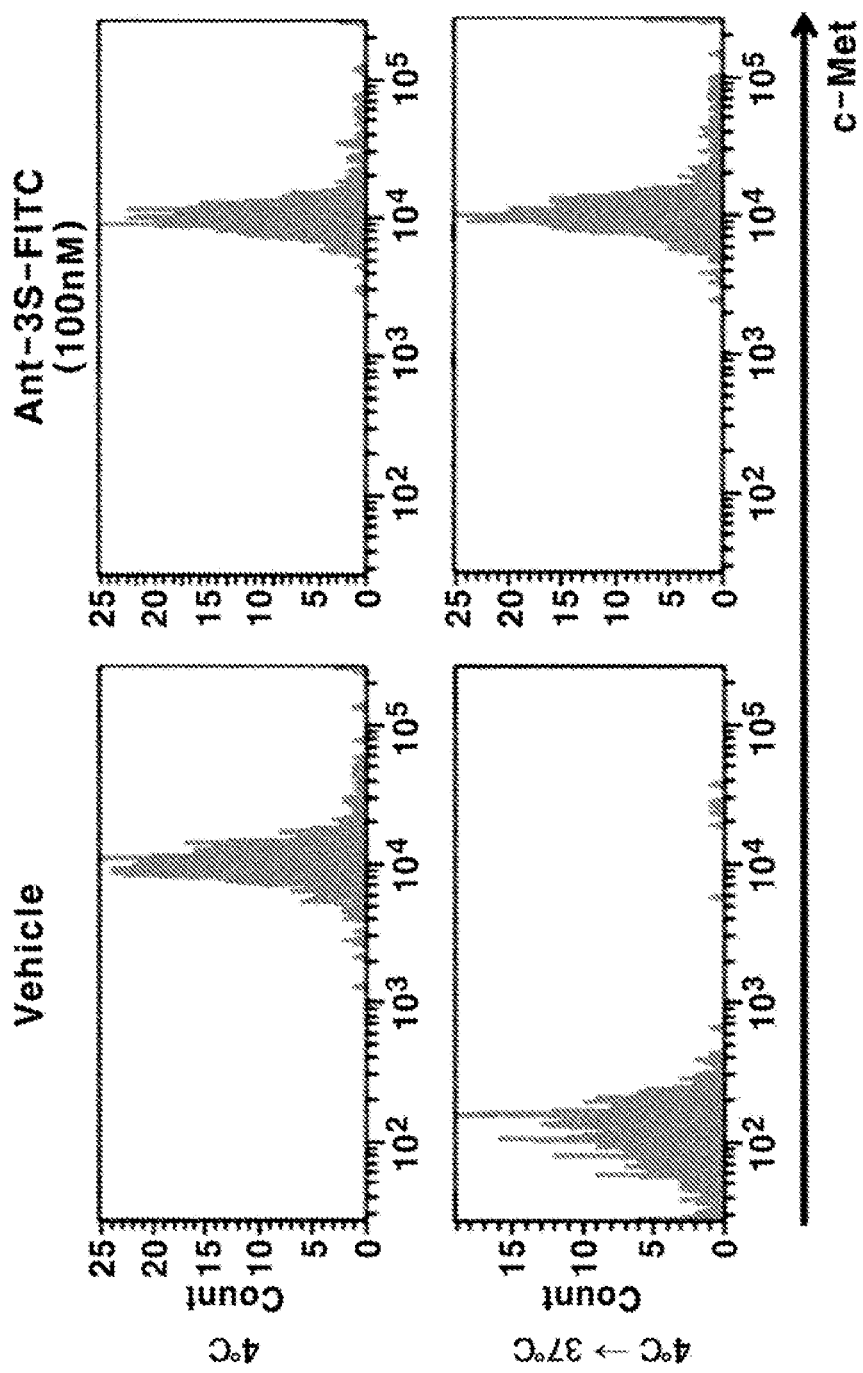
FIG. 9 is FACS data (FIG. 9a) and fluorescence microscopic images (FIG. 9b) showing inhibition of c-Met endocytosis by Ant-3S-FITC fusion polypeptide.
Figure 10A:
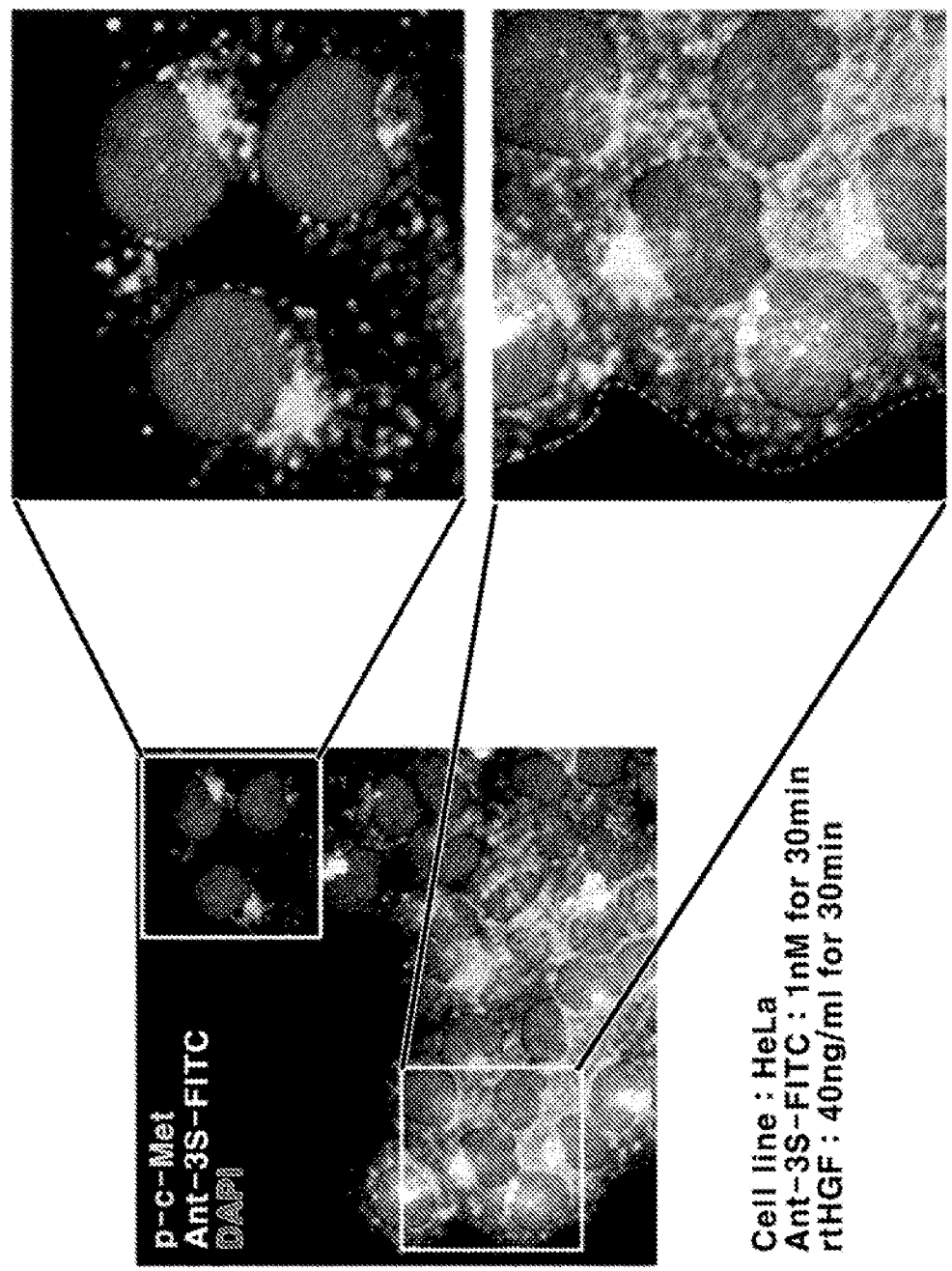
FIG. 10 is fluorescence microscopic images showing that Ant-3S-FITC fusion polypeptide can inhibit HGF-dependent endocytosis of phosphorylated c-Met in HeLa (FIG. 10a) and Hep3B (FIG. 10b) cells.
Figure 10B:
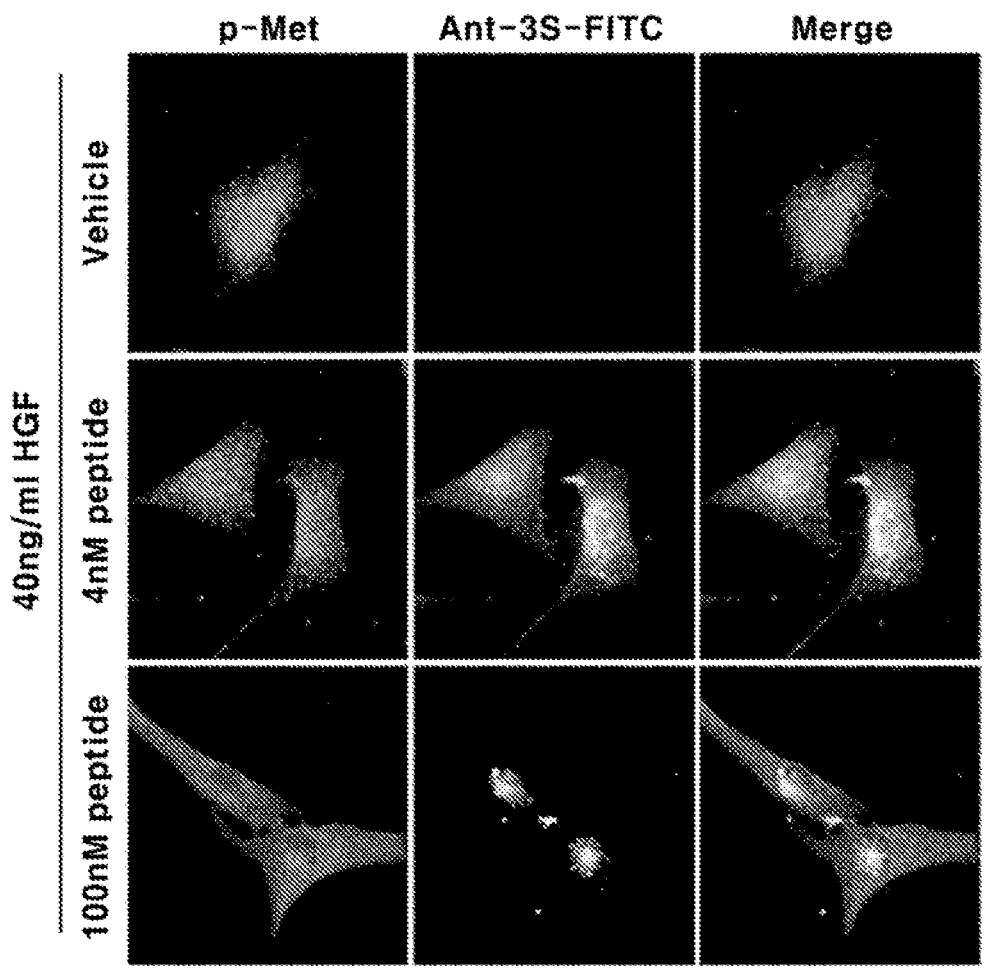

In one embodiment of the present invention, FACS and fluorescence microscopy were performed to examine inhibition of c-Met endocytosis by Ant-3S-FITC fusion polypeptide (FIGS. 9a and 9b), and fluorescence microscopy was also performed to examine that endocytosis of HGF-induced phosphorylated c-Met was inhibited (FIGS. 10a and 10b). Further, Western blotting was performed to examine that autophosphorylation of c-Met was inhibited by the fusion polypeptide (FIG. 11).

In still another aspect, the present invention provides a pharmaceutical composition for preventing or treating cancer comprising the endocytic motif represented by the amino acid sequence of SEQ ID NO. 1 as an active ingredient.

In still another aspect, the present invention provides a pharmaceutical composition for preventing or treating cancer comprising the fusion polypeptide that is represented by N terminus-protein transduction domain-polypeptide including endocytic motif represented by amino acid sequence of SEQ ID NO. 1-C terminus or N terminus-polypeptide including endocytic motif represented by amino acid sequence of SEQ ID NO. 1-protein transduction domain-C terminus, as an active ingredient.

In still another aspect, the present invention provides a method for preventing or treating cancer comprising the step of administering the composition to a subject having cancer or being at risk of having cancer.

The pharmaceutical composition may have an inhibitory effect on cancer metastasis or growth.

As used herein, the term "cancer" refers to a disease associated with cell death regulation, and caused by excessive proliferation resulting from disruption of normal balance of apoptosis. Occasionally, the abnormal excessive cell proliferation invades nearby tissues and organs to form a tumor, which destroys or deforms normal parts of the body. This state is called cancer.

Preferably, the cancer may be cancer where the signaling pathway of HGF and its receptor c-Met is activated, and the cancer may be, but is not limited to, one or more cancers selected from the group consisting of ovarian cancer, breast cancer, osteosarcoma, colon cancer, esophageal cancer, duodenal cancer, renal cancer, lung cancer, pancreatic cancer, gastric cancer, cervical cancer, and prostate cancer.

As used herein, the term "prevention" refers to all of the actions by which metastasis or growth of cancer is restrained or retarded by administration of the composition, and the term "treatment" refers to all of the actions by which the symptoms of cancer have taken a turn for the better or been modified favorably by administration of the composition.

As used herein, the term "subject" means all animals including human having cancer or being at risk of having cancer, and the cancer can be effectively prevented or treated by administering the composition of the present invention to the subject. The composition of the present invention may be administered in combination with the conventional anticancer agent.

The pharmaceutical composition may be administered via any of the common routes, as long as it is able to reach a desired tissue. The composition of the present invention may be administered via an intraperitoneal, intravenous, intramuscular, subcutaneous, intradermal, oral, intranasal, intrapulmonary or intrarectal route depending on the desired purpose, but are not limited thereto. In addition, the composition may be administered by any device capable of delivering the active ingredient to the target cell.

The composition of preventing or treating cancer of the present invention may include a pharmaceutically acceptable carrier. The composition including the pharmaceutically acceptable carrier may be prepared in a variety of oral or parenteral formulations. For preparation into various formulations, a diluent or an excipient, such as a typical filler, a bulking agent, a binder, a wetting agent, a disintegrating agent, or a surfactant, may be used. Examples of a solid formulation for oral administration include tablets, pills, powder, granules, and capsules, and these solid formulations are prepared by mixing one or more compounds with at least one excipient, for example, starch, calcium carbonate, sucrose, lactose, or gelatin. In addition to the excipient, a lubricant, such as magnesium stearate, or talc, is used. As a liquid formulation for oral administration, a suspension, a liquid for internal use, an emulsion, a syrup or the like may be used, and in addition to water, which is often used, and liquid paraffin, various other excipients, for example, a wetting agent, a sweetener, a flavoring agent, a preserving agent or the like may be included. As a formulation for parenteral administration, a sterilized liquid solution, a non-aqueous solvent, a suspension, an oil, a lyophilized preparation, a suppository formulation or the like may be used. As a non-aqueous solvent or a suspension, propylene glycol, polyethylene glycol, a plant oil such as olive oil, an injectable ester such as ethylolate or the like may be used. As a base for suppositories, witepsol, macrogol, TWEEN 61, cacao butter, laurin butter, glycerogelatin or the like may be used.

The pharmaceutical composition may have any one formulation selected from the group consisting of a tablet, a pill, a powder, a granule, a capsule, a suspension, a liquid for internal use, an emulsion, a syrup, a sterilized liquid solution, a non-aqueous solvent, a suspension, an emulsion, a lyophilized preparation, and a suppository formulation.

The composition of the present invention may be administered in a pharmaceutically effective amount, and as used herein, the phrase "pharmaceutically effective amount" refers to an amount sufficient to treat the disease at a reasonable benefit/risk ratio applicable to any medical treatment. An effective dose level may vary depending on a variety of factors including the type, severity, age, and sex of the subject, drug activity, drug sensitivity, administration time, administration route, discharge ratio, treatment period, and co-administered drugs, and other factors well known in the medical field. The composition of the present invention may be administered alone or in combination with other therapeutics. The co-administration of the composition of the present invention with other therapeutics may be carried out simultaneously or sequentially. Single or multiple dosages are possible. It is important to use the composition in the minimum possible amount sufficient to obtain the greatest therapeutic effect without side effects, considering all the factors.

The composition of the present invention may be used alone, or in combination with surgery, hormone therapy, chemical therapy, and a biological response regulator in order to prevent or treat cancer.

Figure 14:
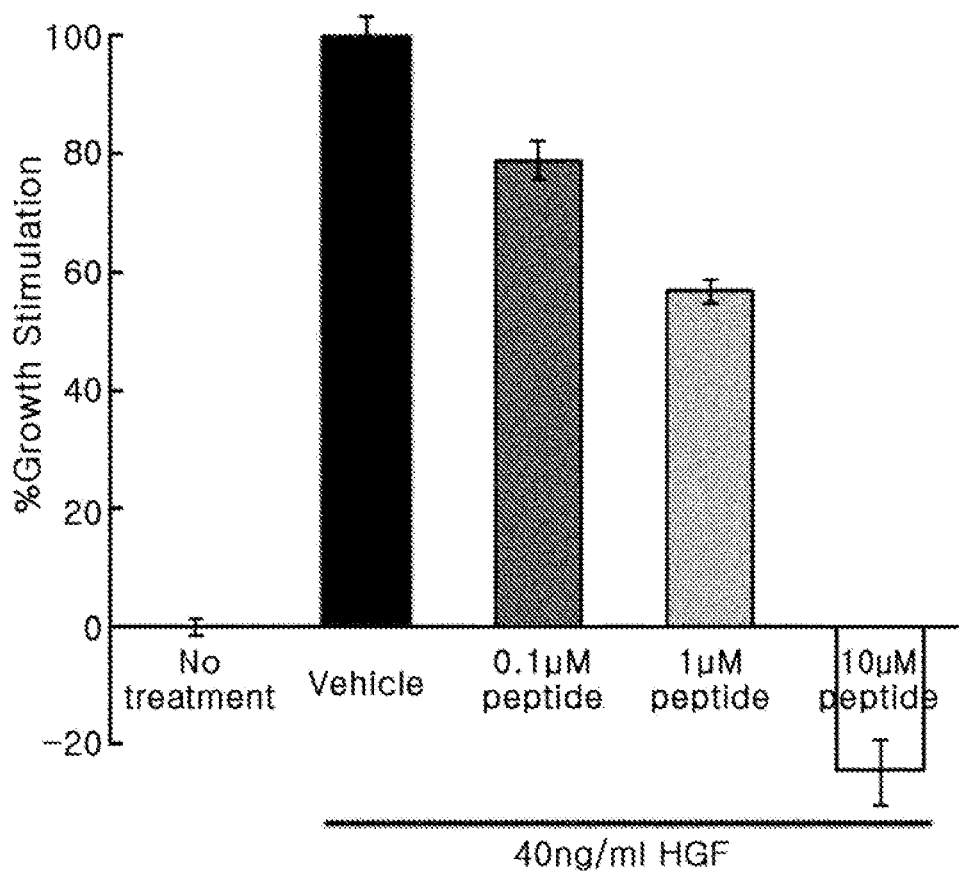
FIG. 14 is a graph of the result of MTT assay showing that Ant-3S-FITC fusion polypeptide can inhibit proliferation of Hep3B cell line.
Figure 15:
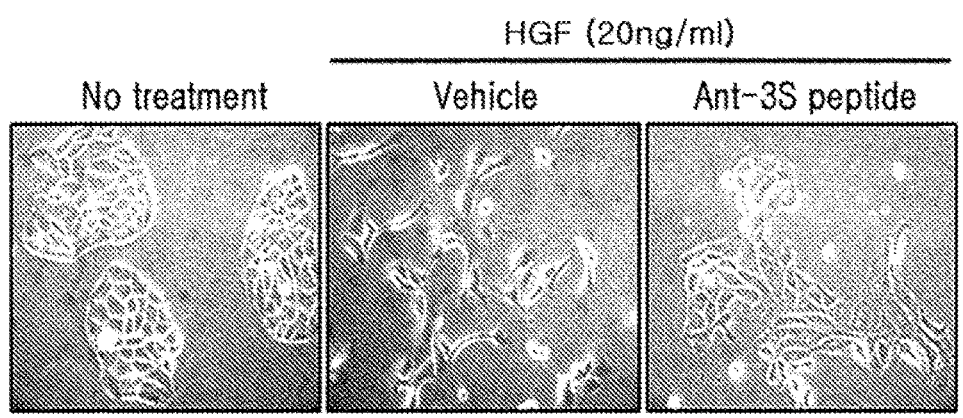
FIG. 15 is an image showing that Ant-3S-FITC fusion polypeptide can inhibit HGF-induced scattering of MDCK cell line.
Figure 16A:
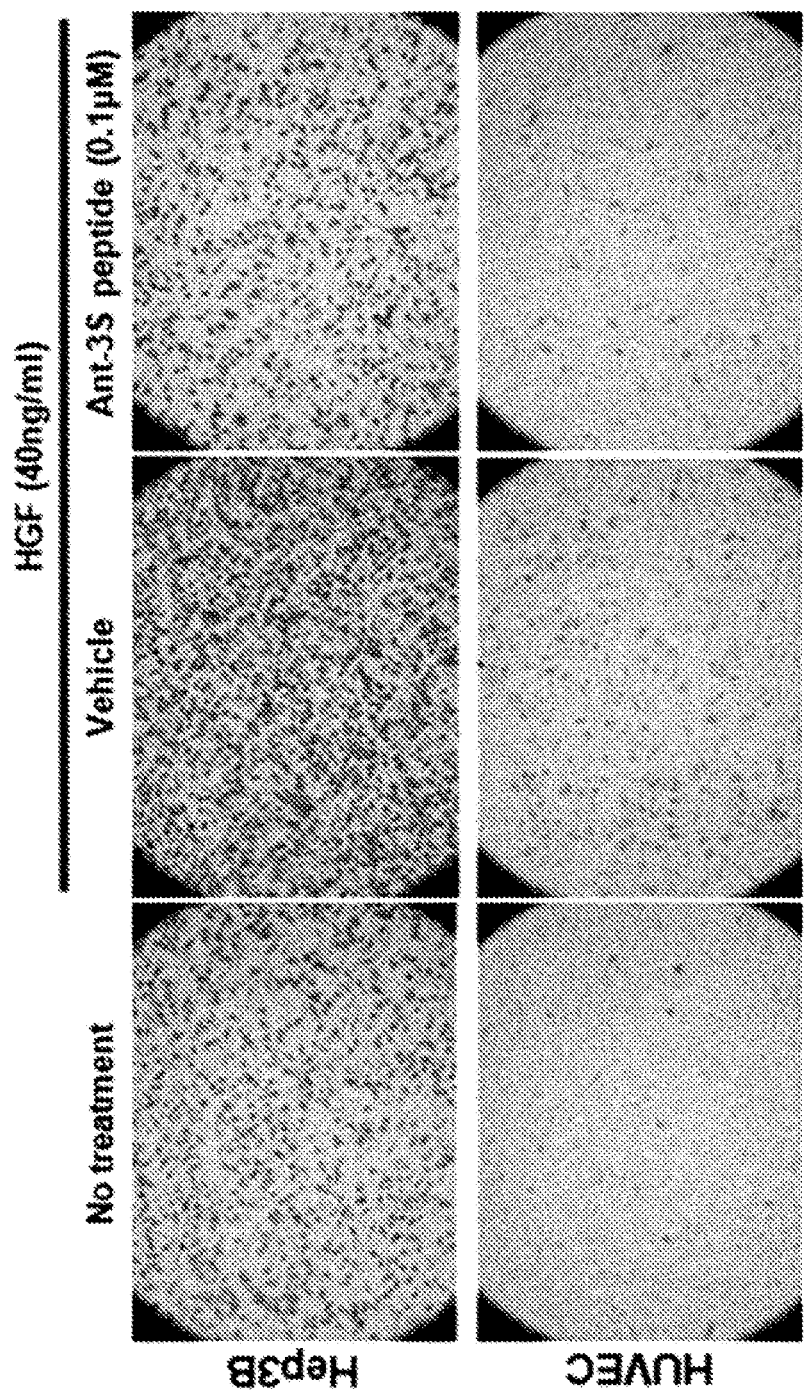
FIG. 16 is an image (FIG. 16a) and a graph (FIG. 16b) of the result of a TRANSWELL migration assay showing that Ant-3S-FITC fusion polypeptide can inhibit migration of HUVEC (human umbilical vein endothelial cell) and Hep3B cell.
Figure 16B:
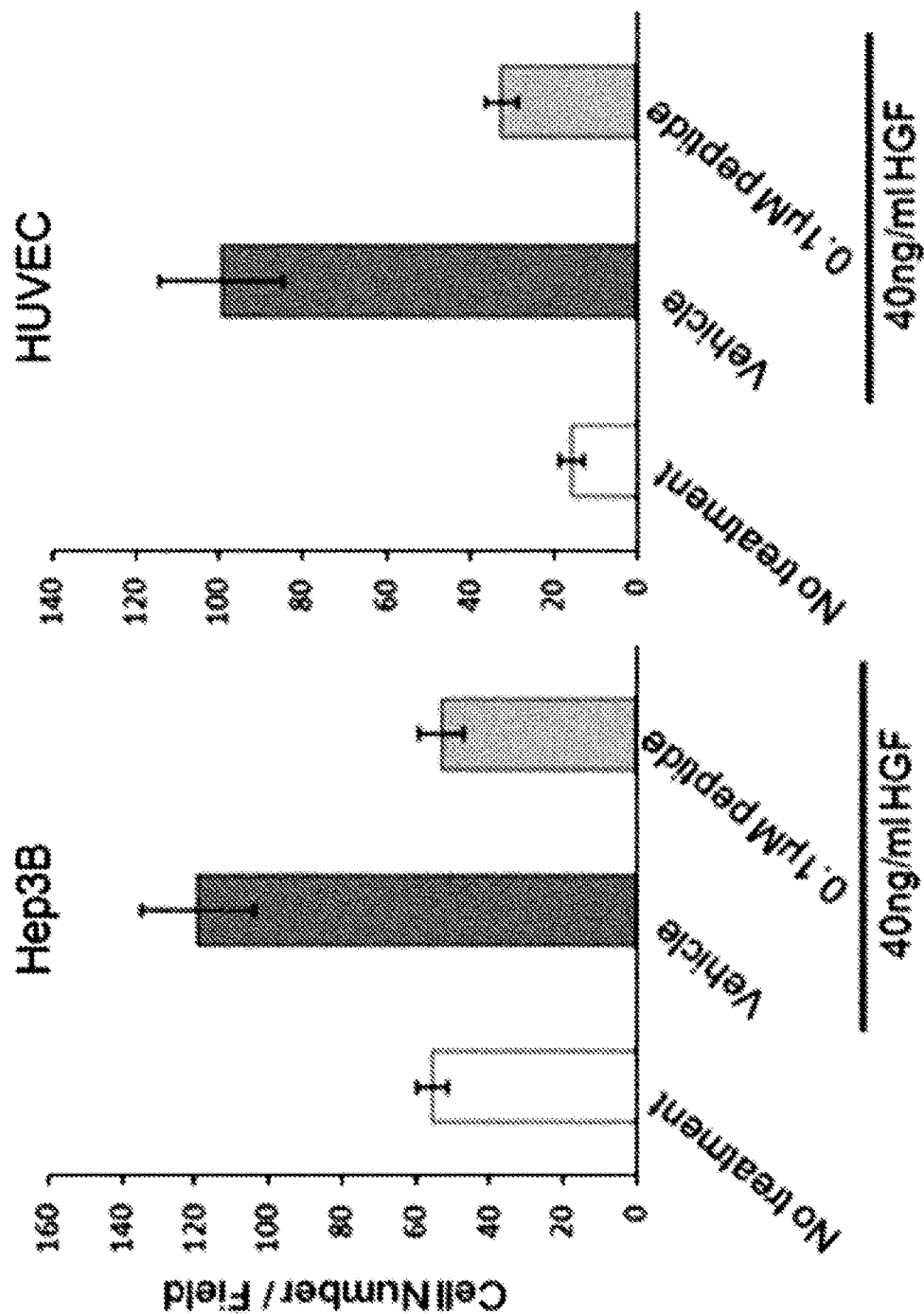

In one embodiment of the present invention, it was confirmed that the fusion polypeptide of the present invention specifically inhibits endocytosis of c-Met or phosphorylated c-Met (FIGS. 9a, 9b, 10a, 10b and 17), and MTT assay showed that the fusion polypeptide is able to inhibit proliferation of cancer cell line (FIG. 14). Further, TRANSWELL migration assay and scattering assay showed that the fusion polypeptide is able to inhibit HGF-dependent migration of cancer cell line (FIGS. 15, 16a and 16b). Consequently, the pharmaceutical composition including the fusion polypeptide as an active ingredient can be used for the prevention and treatment of cancer.

MODE FOR INVENTION

Hereinafter, the present invention will be described in detail with reference to Examples. However, the following Examples are for illustrative purposes only, and the invention is not intended to be limited by these Examples.

EXAMPLE 1

Cell Culture and Transfection

HUVEC, Hep3B, HeLa, COS-7 and MDCK cell lines were cultured in DMEM (Thermo, SH30243.01) containing 10% FBS (Thermo, SH30532.03) and 1% penicillin/streptomycin (streptomycin; Thermo, SV30010) under the conditions of 5% $CO_2$ and 37° C. For suspension, HUVEC, HeLa and Hep3B cells were treated with 0.05% TRYPSIN (Thermo, SH30236.01), and then left at 37° C. for 5 minutes. For transfection, a mixture of 1.5 μg of plasmid DNA and 3 μl of LIPOFECTAMINE (INVITROGEN, 11668-027) in 0.2 ml of serum-free DMEM was left at room temperature. After 25 minutes, when cells were grown to 50% confluency in 6-well plates, the medium was replaced with serum-free DMEM, and the cells were treated with the mixture. After 5 hours, the medium was replaced with DMEM containing 10% FBS. After 48 hours, the cells were used for fluorescence microscopy.

EXAMPLE 2

Experimental Methods 2-1. Flow Cytometry

In order to examine rapid internalization of Ant-3S-FITC fusion polypeptide of the present invention in cells, HeLa cells were suspended by treatment with 0.05% TRYPSIN, and washed with PBS once, and then suspended with 100 nM Ant-3S-FITC fusion polypeptide (in serum-free DMEM). Thereafter, the cells were cultured over time at 5% $CO_2$ and 37° C., and then washed with PBS three times, and fluorescence intensity was measured through FACS (BD CantoII Flow Cytometer).

In order to examine whether Ant-3S-FITC fusion polypeptide inhibits c-Met endocytosis in HeLa cells, HeLa cells were suspended by treatment with 0.05% TRYPSIN, and washed with DPBS once, and then suspended with 100 nM Ant-3S-FITC fusion polypeptide (in serum-free DMEM). Thereafter, the cells were cultured for 30 minutes at 5% $CO_2$ and 37° C., and then transferred at 4° C. and left for 30 minutes to block endocytosis. To induce endocytosis again, the cells were transferred again at 5% $CO_2$ and 37° C., and left for 30 minutes. For fixation, the cells were left in cold methanol at −20° C. for 10 minutes. For staining of c-Met, anti-c-Met antibody (R&D SYSTEMS, AF-276) was diluted in PBA buffer (1% BSA in PBS buffer) at a concentration of 2 μg/ml, and the cells were suspended therein, and reacted at 4° C. for 30 minutes. The cells were washed with PBS (Phosphate buffered saline) once, and for secondary antibody treatment, anti-goat IgG ALEXA FLUOR 568 (INVITROGEN, A-11079) was diluted at a ratio of 1:200 and treated to the cells at 4° C. for 30 minutes. Then, the cells were washed with PBS twice, and fluorescence intensity was measured using FACS (BD CantoII Flow Cytometer).

2-2. Immunofluorescence Microscopy

<2-2-1> Quantitation of Endocytosis Percentage

Each of plasmid DNAs encoding Tac chimeric proteins illustrated in FIG. 2 was expressed in COS-7 cell line to induce endocytosis. To quantify endocytosis percentage, the following method was used. First, plasmid DNA was transfected into COS-7 cell line, and next day, cells were suspended in DMED supplemented with 10% FBS, and seeded onto an 8-well slide glass (Thermo, 154534) to 50% confluency. Next day, to block endocytosis, cells were transferred at 4° C. and left for 30 minutes. Anti-Tac (BD BIOSCIENCES, 347640) antibody was diluted in DMEM supplemented with 10% FBS at a ratio of 1:10, and treated at 4° C. for 30 minutes. The cells were washed with medium three times. To induce endocytosis again, the cells were transferred at 5% $CO_2$ and 37° C., and left for different time periods. The cells were fixed in 4% paraformaldehyde for 45 minutes at room temperature. To detect cell surface anti-Tac antibody, anti-mouse IgG-ALEXA FLUOR 488 (INVITROGEN, A-11001) was diluted with PBS containing 3% normal goat serum (Vector, S-1000) at a ratio of 1:500, and treated at room temperature for 1 hour. Then, the cells were washed with PBST for 5 minutes three times. For permeablization and blocking, the cells were treated with PBST containing 3% normal goat serum at room temperature for 1 hour. Next, to detect intracellular Tac, anti-mouse IgG-ALEXA FLUOR 568 (INVITROGEN, A11061) was diluted with PBST containing 3% normal goat serum at a ratio of 1:500, and treated at room temperature for 1 hour. The cells were washed with PBST three times, and mounted in Mounting Medium with DAPI (Vector, H-1200). Next day, the sample was examined by fluorescence microscopy (Olympus IX2-UCB). For treatment of inhibitors, 100 μg/ml ConA (SIGMA, C0412), 80 μM Dynasore (SIGMA, D7693), 1 μM Go6976 (CALBIOCHEM, 365250), 1 μM K252a (INVITROGEN, PHZ1131) and 1 μM Vinblastine (SIGMA, V1377) were pretreated at 5% $CO_2$ and 37° C. for 30 minutes, before endocytosis assay.

<2-2-2> Analysis on Internalization of Ant-3S-FITC Fusion Polypeptide in Cells

In order to examine rapid internalization of Ant-3S-FITC fusion polypeptide in cells, HeLa cells were suspended by treatment with 0.05% TRYPSIN, and then suspended in DMEM supplemented with 10% FBS, and seeded onto an 8-well slide glass (Thermo, 154534) to 50% confluency. Next day, the cells were washed with DPBS once, and then treated with 100 nM Ant-3S-FITC fusion polypeptide (in DMEM containing 10% FBS) at 5% $CO_2$ and 37° C. for 30 minutes. Thereafter, to block endocytosis, the cells were transferred at 4° C. and left for 30 minutes. To induce endocytosis again, the cells were transferred again at 5% $CO_2$ and 37° C., and left for 30 minutes. The cells were fixed in 4% paraformaldehyde for 45 minutes at room temperature. For staining of cell surface c-Met, anti-c-Mat antibody (R&D SYSTEMS, AF-276) was diluted in PBA buffer (1% BSA in PBS buffer) at a concentration of 2 μg/ml, and treated to the cells, and reacted at 4° C. for 30 minutes. The cells were washed with PBS once, and for secondary antibody treatment, anti-goat IgG ALEXA FLUOR 568 (INVITROGEN, A-11079) was diluted at a ratio of 1:500 and treated to the cells at 4° C. for 30 minutes. Then, the cells were washed with PBS three times, and mounted in Mounting Medium with DAPI (Vector, H-1200). Next day, the sample was examined by fluorescence microscopy (Olympus IX2-UCB).

<2-2-3> Inhibition of HGF-dependent Endocytosis of Phosphorylated c-Met by Ant-3S-FITC Fusion Polypeptide In order to examine whether Ant-3S-FITC fusion polypeptide inhibits HGF-dependent endocytosis of phosphorylated c-Met (Phospho-c-Met) in HeLa and Hep3B cell lines, HeLa and Hep3B cells were suspended by treatment with 0.05% TRYPSIN, and then suspended in DMEM supplemented with 10% FBS, and seeded onto an 8-well slide glass (Thermo, 154534) to 50% confluency. Next day, cells were starved in serum-free DMEM for 24 hours. Next day, cells were washed with DPBS once, and then Ant-3S-FITC fusion polypeptide was diluted with serum-free DMEM at various concentrations, and treated to the cells at 5% $CO_2$ and 37° C. for 30 minutes. Thereafter, to induce endocytosis by HGF, 40 ng/ml of recombinant human HGF (R&D SYSTEMS, 294-HG-005) was treated to the cells at 5% $CO_2$ and 37° C. for 30 minutes. The cells were fixed in 4% paraformaldehyde for 45 minutes at room temperature, and washed with PBST (0.2% TRITON-X100 in PBS) three times. For permeablization and blocking, the cells were treated with PBST containing 3% normal goat serum at room temperature for 1 hour. For staining of phosphorylated c-Met, anti-p-Met antibody (INVITROGEN, 44888G) was diluted in 3% normal goat serum (in PBST) at a ratio of 1:1000, and treated to the sample at 4° C. for 16 hours. The cells were washed with PBST three times, and for secondary antibody treatment, anti-rabbit IgG ALEXA FLUOR 568 (INVITROGEN, A-11036) was diluted at a ratio of 1:500 and treated to the cells at room temperature for 1 hour. Then, the cells were washed with PBST three times, and mounted in Mounting Medium with DAPI (Vector, H-1200). Next day, the sample was examined by fluorescence microscopy (Olympus IX2-UCB).

<2-2-4> Effect of Ant-3S-FITC Fusion Polypeptide on Other Receptor Endocytosis

In order to examine whether Ant-3S-FITC fusion polypeptide affects endocytosis of other receptors than c-Met, plasmid DNAs prepared by cloning Tac/3S, Tac/PSD-95 and GLUT4-HA proteins into pcDNA3.1 were transfected into COS-7 cell line. Next day, the cells were suspended in DMEM supplemented with 10% FBS, and seeded onto an 8-well slide glass (Thermo, 154534) to 50% confluency. Next day, cells were washed with DPBS once, and then treated with 100 nM Ant-3S-FITC fusion polypeptide (in DMEM containing 10% FBS) at 5% $CO_2$ and 37° C. for 30 minutes. Then, to block endocytosis, the cells were transferred at 4° C. and left for 30 minutes. Anti-HA (INVITROGEN, 71-5500) antibody and anti-Tac (BD BIOSCIENCES, 347640) antibody were diluted in DMEM containing 10% FBS at a ratio of 1:100 and 1:10, respectively, and treated to the cells at 4° C. for 30 minutes. The cells were washed with DMEM containing 10% FBS three times. To induce endocytosis again, the cells were transferred again at 5% $CO_2$ and 37° C., and left for 30 minutes. The cells were fixed in 4% paraformaldehyde for 45 minutes at room temperature, and washed with PBST (0.2% TRITON-X100 in PBS) three rimes. For permeablization and blocking, the cells were treated with PBST containing 3% normal goat serum at room temperature for 1 hour. For secondary antibody treatment, anti-rabbit IgG ALEXA FLUOR 568 (INVITROGEN, A-11036) and anti-mouse IgG ALEXA FLUOR 568 (INVITROGEN, A-11061) were diluted at a ratio of 1:500 and treated to the cells at room temperature for 1 hour. Then, the cells were washed with PBST three times, and mounted in Mounting Medium with DAPI (Vector, H-1200). Next day, the sample was examined by fluorescence microscopy (Olympus IX2-UCB).

2-3. Western Blot

Hep3B cell line was seeded onto a 6-well plate to 70% confluency. Next day, the medium was replaced with serum-free DMEM. Next day, the cells were washed with serum-free DMEM once. Then, Ant-3S-FITC fusion polypeptide was diluted in serum-free DMEM at various concentrations, and treated to the cells at 5% $CO_2$ and 37° C. for 30 minutes.

Thereafter, to activate signal transduction by HGF, the cells were treated with 40 ng/ml of recombinant human HGF (R&D SYSTEMS, 294-HG-005) at 5% $CO_2$ and 37° C. for 30 minutes.

Thereafter, the plate was transferred onto ice and washed with cold PBS three times. Then, cells were collected using a cell scraper, and treated with an RIPA lysis buffer containing a protease inhibitor cocktail (CALBIOCHEM, 11836153001) and a phosphatase inhibitor cocktail (SIGMA, P5726), and left on ice for 30 minutes. The cells were centrifuged using a centrifuge at 13000 rpm for 20 minutes. The supernatant was transferred to a new e-tube, and a 5× sample buffer was added thereto, and denatured in boiling water for 10 minutes. The cell lysate thus obtained was electrophoresed in a 8% Tris-HCl SDS gel at 100 volt for 1 hour and 30 minutes, and transferred onto a nitrocellulose membrane at 100 volt for 1 hour. The membrane was put in 5% skim milk in TBST (0.05% T-TWEEN in PBS) and blocked at room temperature for 1 hour with shaking. The membrane was treated with primary antibody diluted in 5% skim milk in TBST at 4° C. for 16 hours with shaking. The membrane was transferred at room temperature and washed with TBST for 10 minutes three times. Then, the membrane was treated with secondary antibody diluted in 5% skim milk in TBST at room temperature for 1 hour with shaking. Again, the membrane was washed with TBST for 10 minutes three times, and developed using an ECL detection reagent (Intron, 16033). As the primary antibody, anti-p-Met antibody (INVITROGEN, 44888G), anti-p-FAK antibody (Cell signaling, 3283S), anti-p-AKT antibody (Millipore, 05-736), anti-p-Erk1/2 (Cell signaling, 9101S) and anti-β-actin antibody (SIGMA, A5441) were used, and as secondary antibody, anti-rabbit IgG-HRP (Santacruz, sc-2004) and anti-mouse IgG-HRP (Santacruz, sc-2005) were used.

2-4. Wound Healing Assay

Hep3B cell line was seeded onto a 6-well plate to 90% confluency. Next day, the cells were washed with DPBS once, and the medium was replaced with serum-free DMEM. Next day, the cells were wounded by making scratches with a 200 μl-yellow tip. Then, cells were washed with serum-free DMEM once. Ant-3S-FITC fusion polypeptide was diluted in serum-free DMEM at various concentrations, and then treated to the cells at 5% $CO_2$ and 37° C. for 30 minutes. To activate signal transduction by HGF, the cells were treated with 40 ng/ml of recombinant human HGF (R&D SYSTEMS, 294-HG-005), and after 24 hours, wound healing was examined under a microscope.

2-5. TRANSWELL Migration Assay

The upper chamber of TRANSWELL (Corning, 3422) was blocked with 100 μl of 0.1% BSA (in PBS; 1 mg/ml) at 37° C. for 1 hour, and washed with PBS once. Hep3B cells treated with Ant-3S-FITC fusion polypeptide for 30 minutes were suspended in 0.1% BSA (in PBS), and plated onto the upper chamber at a density of 1×10⁴ per well (in 100 μl). 500 μl of 40 ng/ml recombinant human HGF (R&D SYSTEMS, 294-HG-005) was added to the lower chamber. Incubation was performed at 37° C. for 16 hours, and the upper chamber was washed with PBS once, and then incubated in crystal violet at RT for 10 minutes. Thereafter, the upper chamber was washed with distilled water, and cells at the top side were removed with a cotton swab, and observed under a microscope.

2-6. MTT Assay

Hep3B cell line was seeded onto 96-well plate at a density of 5×10³ cells/well. Next day, the medium was replaced with serum-free DMEM for starvation. Next day, Ant-3S-FITC fusion polypeptide was diluted in serum-free DMEM at various concentrations, and treated to the cells at 37° C. for 30 minutes. Then, a mixture of 2% FBS+Ant-3S-FITC fusion polypeptide was added thereto. After 3 days, 20 μl of MTT per 100 μl was added to each well, and incubated at 37° C. for 1 hour. After completely removing the supernatant, absorbance at 560 nm was measured.

2-7. Co-Immunoprecipitation

Plasmid DNAs encoding Tac/3S protein and Tac/3S-LL/AA protein were transfected into COS-7 cells using LIPOFECTAMINE, and after 48 hours, an endocytosis assay was performed. In detail, the plate was left at 4° C. for 1 hour, and then transferred at 37° C. and incubated for 10 minutes. Thereafter, the plate was washed with PBS three times, and cells were collected using a cell scraper, and lysed by treatment of 1 ml of NP-40 containing a protease inhibitor cocktail. Then, e-tube containing the lysate was stirred on ice for 30 minutes, and centrifuged at 4° C. and 13000 rpm for 20 minutes. The supernatant was transferred to a new e-tube, and quantified by Bradford assay. 1 mg of the lysate was diluted in 1 ml of lysis buffer. 20 μl of protein G (GE Healthcare, 17-0618-01) slurry was added thereto, and stirred at 4° C. for 10 minutes for pre-clearing (at this time, protein G was washed with PBS three times in advance). Then, centrifugation was performed at 4° C. and 13000 rpm for 10 minutes, and then the supernatant was transferred to a new e-tube, and 4 μg of anti-Tac antibody (BD, 347640) and 20 μl of protein G were added thereto, and stirred at 4° C. for 16 hours. Thereafter, the e-tube was centrifuged at 13000 rpm for 1 minute, and washed with PBS five times. After the last wash, the supernatant was discarded, and the sample buffer was denatured in boiling water for 10 minutes, and then Western blotting was performed. In Western blotting, anti-Tac antibody (Santacruz, sc-665), anti-adaptinβ antibody (BD, 610381) and anti-β-actin antibody (SIGMA, A5441) were used as primary antibody, and anti-rabbit IgG-HRP (Santacruz, sc-2004) and anti-mouse IgG-HRP (Santacruz, sc-2005) were used as secondary antibody.

2-8. MDCK Scattering Assay

MDCK cells were seeded onto a 6-well plate to 30% confluency. Next day, the medium was replaced with FBS-free DMEM. Next day, the Ant-3S-FITC fusion polypeptide was treated thereto at a concentration of 0.1 μM for 90 minutes. Then, recombinant human HGF was treated thereto at a concentration of 20 ng/ml, and after 16 hours, cell morphology was observed under an optical microscope.

2-9. Statistical Analysis of Immunofluorescence Images

To quantify endocytosis of Tac chimeric proteins expressed in COS-7 cells over time, the following Equation was used.

$$*\text{Endocytosis ratio} = 1 - \frac{\text{Surface } Tac}{\text{Total } Tac} = 1 - \frac{\text{Green} + \alpha}{\text{Green} + \text{Red}} \quad \text{[Equation 1]}$$

$\alpha$ = surface $Tac$ detected by Red fluorescence
= 0.429 − fold intensity of Green fluorescence
(by 0 minute Endocytosis standard)

Figure 3B:
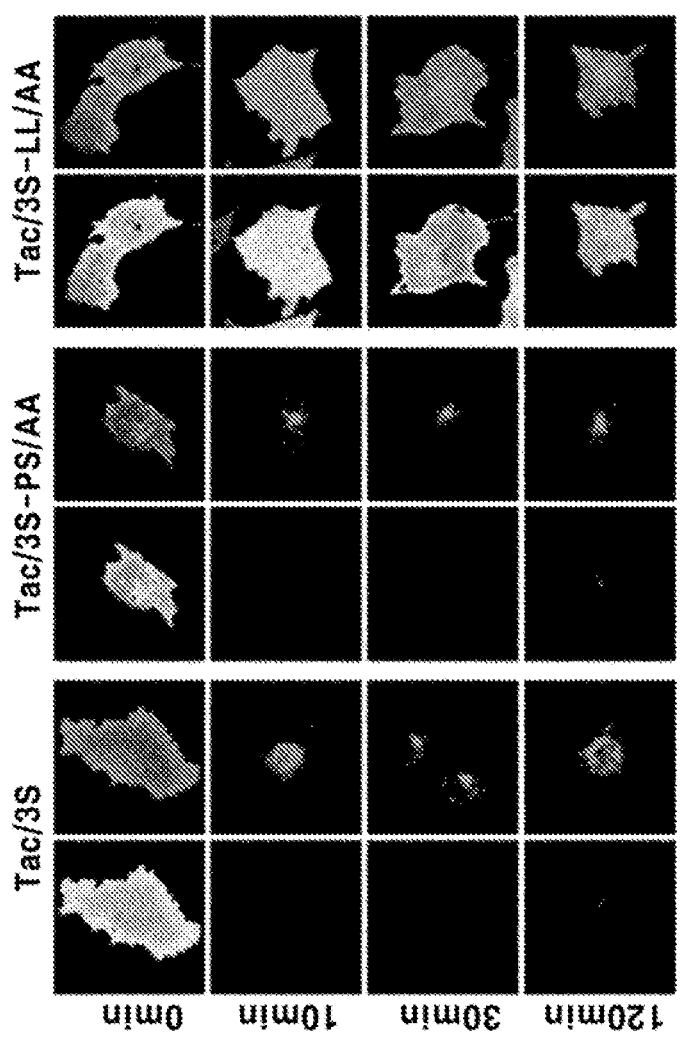
Figure 4A:
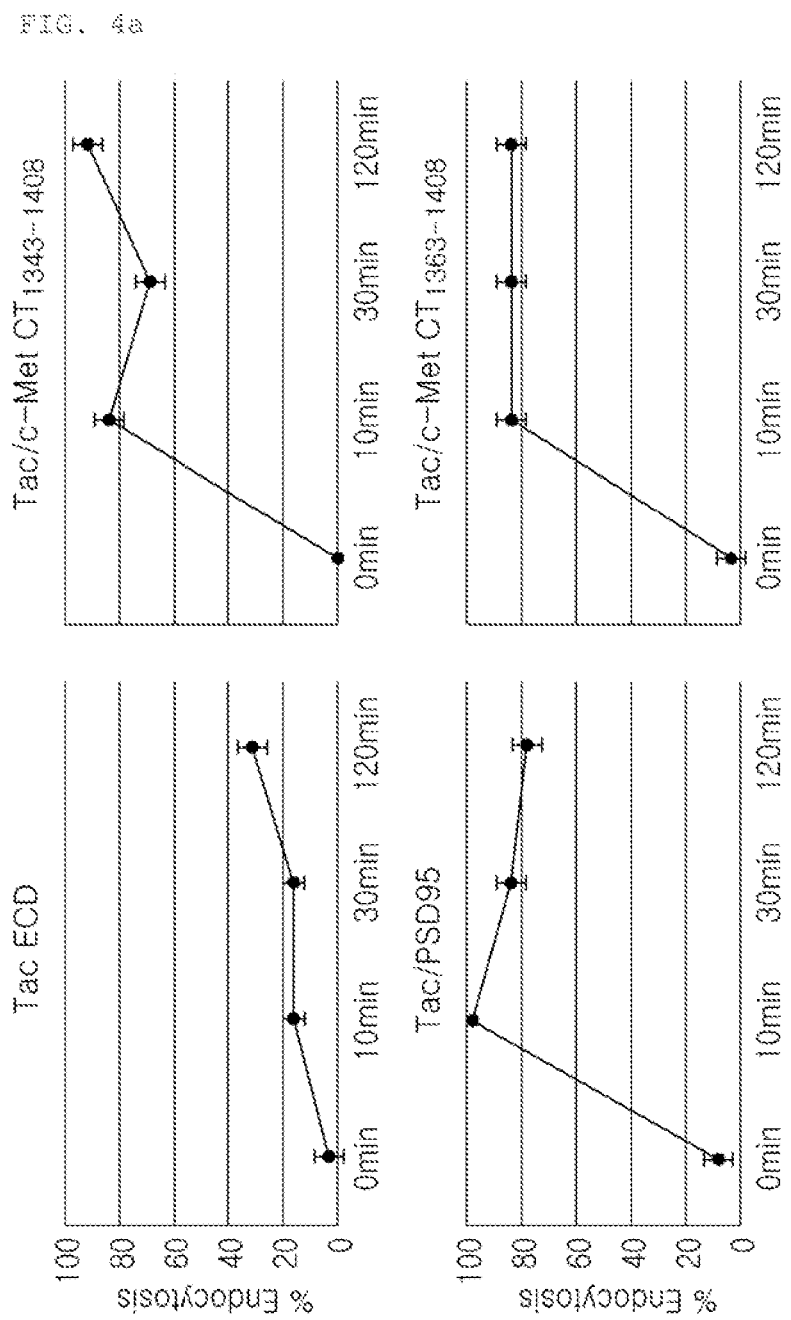
FIGS. 4a and 4b are graphs showing quantitation of endocytosis of FIGS. 3a and 3b.
Figure 4B:
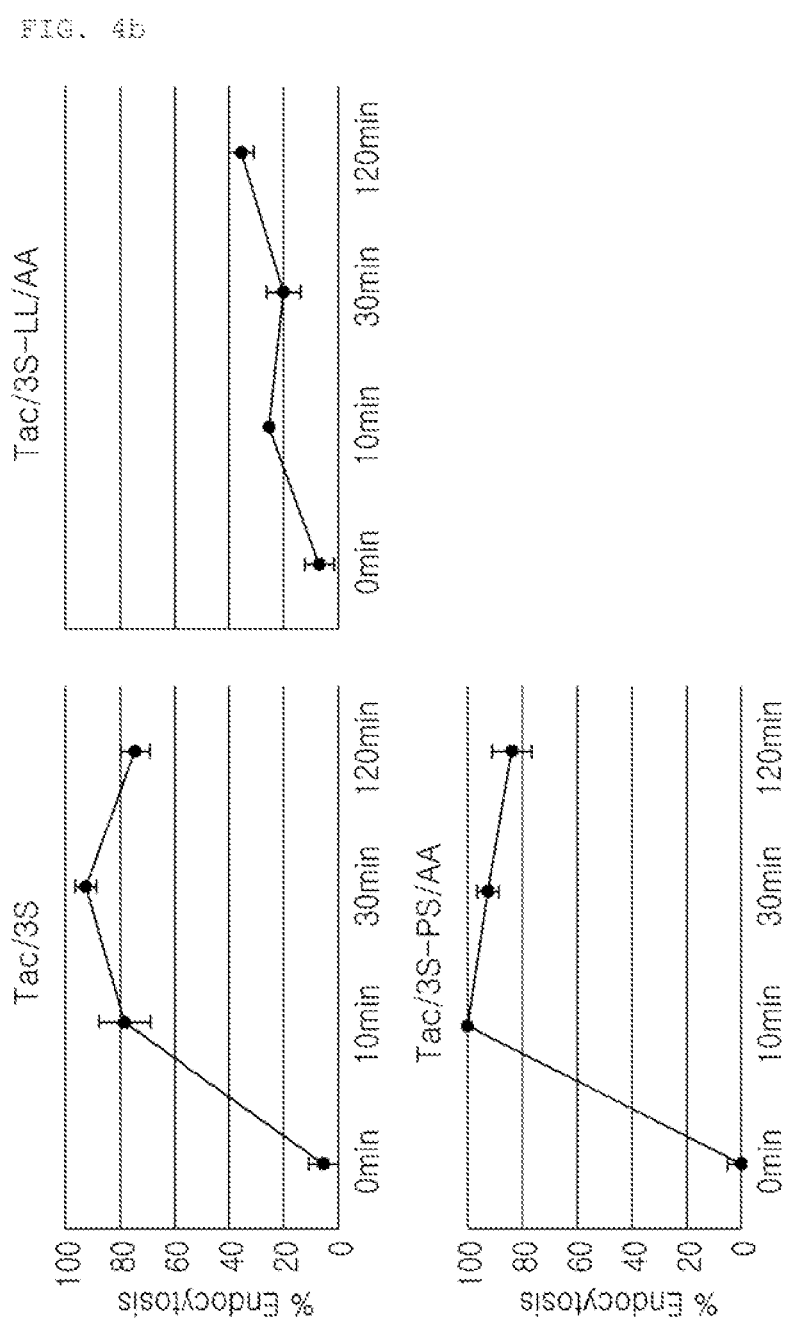

In detail, to detect the surface Tac, Tac was labeled with anti-mouse IgG-ALEXA FLUOR 488 before permeablization, whereas intracellular Tac were labeled with anti-mouse IgG-ALEXA FLUOR 568 after permeablization. As such, green fluorescence intensity indicates the amount of cell surface Tac, and red fluorescence intensity signifies those of endocytosed Tac plus partial cell surface Tac. As the two secondary antibodies used herein are different polyclonal antibodies from each other, detection of surface Tac by the latter labeling with anti-mouse IgG-ALEXA FLUOR 568 may have been partially inhibited by the former labeling with anti-mouse IgG-ALEXA FLUOR 488. Partially detected surface Tac by anti-mouse IgG-ALEXA FLUOR 568 was measured by comparing fluorescence intensity between green and red at 0 min in which no endocytosis occurred. Red fluorescence intensity was 0.429-fold or green fluorescence intensity at 0 min, which was defined as $\alpha$. The endocytosis ratio thus obtained was multiplied by 100 for expression as an endocytosis percentage. Error bar indicates standard deviation. (For statistical analysis, n=6 in FIGS. 4a and 4b, and n=10 in FIG. 5).

EXAMPLE 3

Experimental Results 3-1. Exploration of c-Met Endocytic Motif

In order to examine which amino acids of c-Met mediate endocytosis, DNA constructs shown in FIG. 2 were prepared. In detail, to trace endocytic trafficking, chimeric proteins were prepared by fusion of the extracellular domain (Tac ECD) of TaC(CD25) protein and cytoplasmic domains of c-Met. Because the extracellular domain of Tac itself does not induce endocytosis, c-Met-derived amino acid sequences having different sizes were linked to Tac in order to examine which amino acids are essential for endocytosis. PSD95 has an endocytic motif in the C-terminus, and thus easily endocytosed (Craven et al., J Biol Chem, 275(26): 20045-51, 2000), and a construct prepared by linking the cytoplasmic tail of this protein with Tac was used as a positive control. The plasmid DNAs thus constructed were transiently expressed in COS-7 cells, and the cells were transferred from 4° C. to 37° C. to induce endocytosis. Distribution of the chimeric proteins was observed by microscopy, and shown in FIGS. 3a, 3b, 4a and 4b.

As shown in FIGS. 3a, 3b, 4a and 4b, endocytosis of Tac ECD was not observed even after the lapse of time, but most of Tac/PSD95 was internalized in cells within 10 minutes. Rapid endocytosis of the fusion protein consisting of Tac and the amino acid sequence from 1343 to 1408 of c-Met was observed, and the fusion protein with a shorter amino acid sequence, even with C-terminal 16 amino acids, showed internalization (FIGS. 3a, 3b, 4a and 4b). Because three serine amino acids exist in the C-terminal 16 amino acids of c-Met, the 16 amino acids was designated as 3S, and a polypeptide having 3S sequence was designated as 3S polypeptide.

When dileucine located in 3S was mutated into dialanine, endocytosis of the mutated chimeric protein (Tac/3S-LL/AA) was inhibited (FIGS. 3a and 3b), indicating that dileucine located in the 3S region is a critical motif for endocytic trafficking of c-Met.

3-2. Type of Endocytosis of 3S Polypeptide c-Met is internalized in cells via clathrin-mediated endocytosis, and known to be found in EEA1 and endoplasmic reticulum (Kermorgant et al., J Cell Biol, 182(5):855-63, 2008; Kakazu et al., Invest Ophthalmol Vis Sci, 182(5):855-63, 2008). To demonstrate that 3S polypeptide is the key signal regulating endocytic sorting of c-Met, whether Tac/3S protein is internalized through the pathway like c-Met was examined by fluorescence microscopy in the same manner as in Example 2-2. The results are shown in FIG. 5.

As shown in FIG. 5, when Tac/3S chimeric protein was expressed in COS-7 cells to induce endocytosis, endocytosis was inhibited by ConA (Concannavalin A), Dynasore, and Go6976, whereas endocytosis was not inhibited by K252a and Vinblastine. Endocytosis easily occurs by treatment of Vinblastine, but the transportation of the protein to the perinuclear region was blocked (FIG. 5). It is known that ConA and Dynasore perturb endocytic machinery (Kermorgant et al., EMBO J, 23(19);3721-34, 2004), and Go6976 is a PKC inhibitor involved in c-Met trafficking (Kermorgant et al., J Cell Biol, 182(5):855-63, 2008). In general, when a clathrin coated pit is formed, Dynamin is involved in pinching off the coated pit to form a vesicle (Hinshaw et al., Nature, 374(6518):190-2, 1995). Inhibition of endocytosis of Tac/3S protein by treatment of the Dynamin inhibitor Dynasore indicates internalization of Tac/3S protein through clathrin-mediated endocytosis. The Tac/3S protein traffic also depends on PKC$\alpha$, and is transported to the perinuclear region via microtubule-dependent transport.

Figure 6:
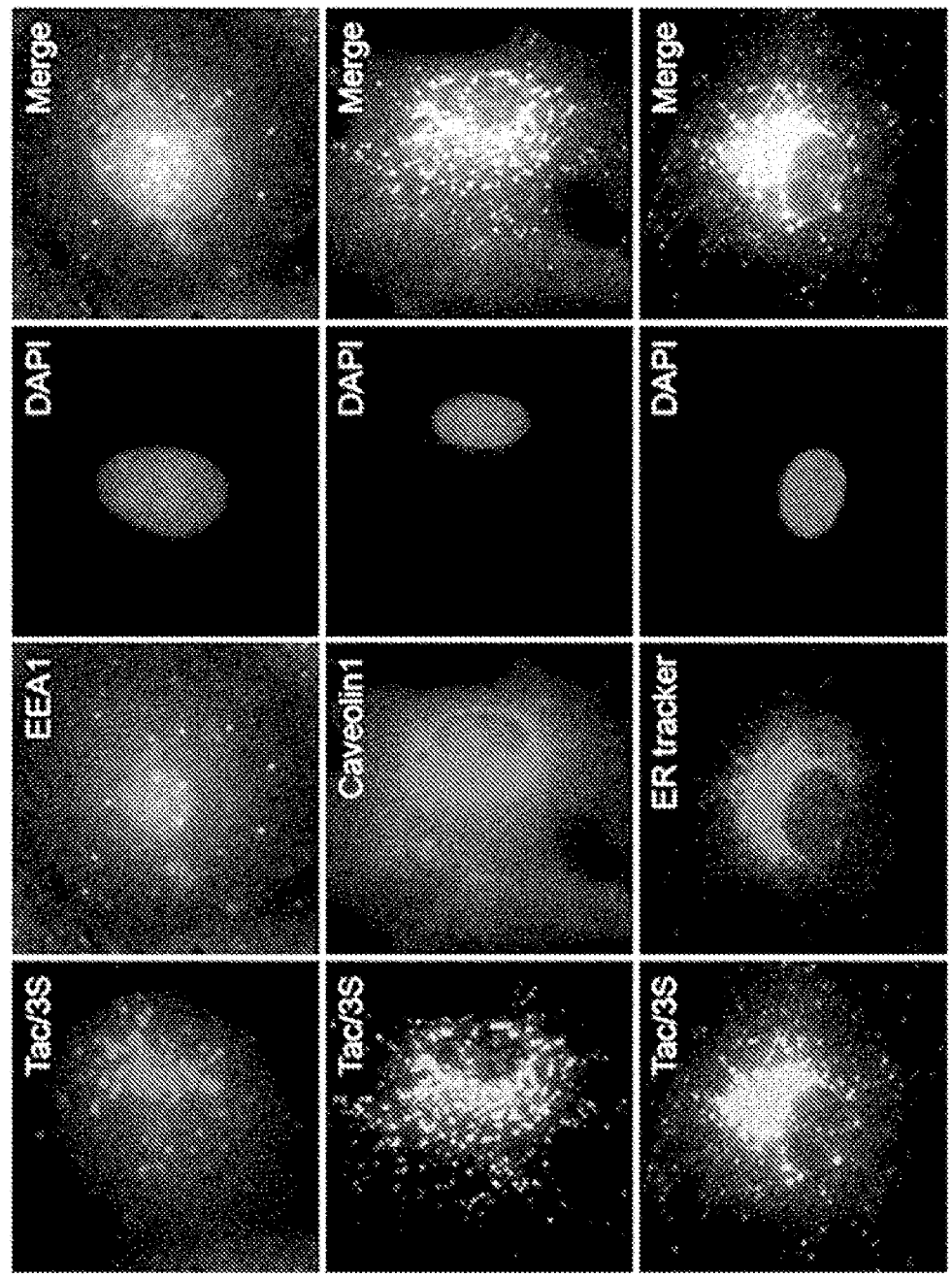
FIG. 6 is a fluorescence microscopic image showing the result of a colocalization test for examining intracellular localization of Tac/3S chimeric protein expressed in COS-7 cells.

Next, fluorescence microscopy was performed in the same manner as in Example 2-2, and a colocalization test was performed to examine subcellular localization of the Tac/3S protein, which is shown in FIG. 6. As shown in FIG. 6, Tac/3S was found to be partially merged with ER tracker (FIG. 6).

3-3. Role of Dileucine Motif on Interaction Between 3S Polypeptide and $\beta$-adaptin It has been known that during the assembly of clathrin-coated vesicle, adaptins specifically bind to cargo receptor by recognizing specific motifs of the receptor's cytoplasmic tail (Kirchhausen et al., Curr Opin Cell Biol, 9(4):488-95, 1997). For example, it has been known that an adaptin $\beta$2 recognizes dileucine of the cargo during GLUT3 endocytosis (Schmidt et al., J Cell Sci, 119(Pt 11):2321-31, 2006). Therefore, in order to examine the interaction of $\beta$-adaptin with dileucine of the 3S polypeptide, co-immunoprecipitation experiment was performed in the same manner as in Example 2-7.

Figure 7:
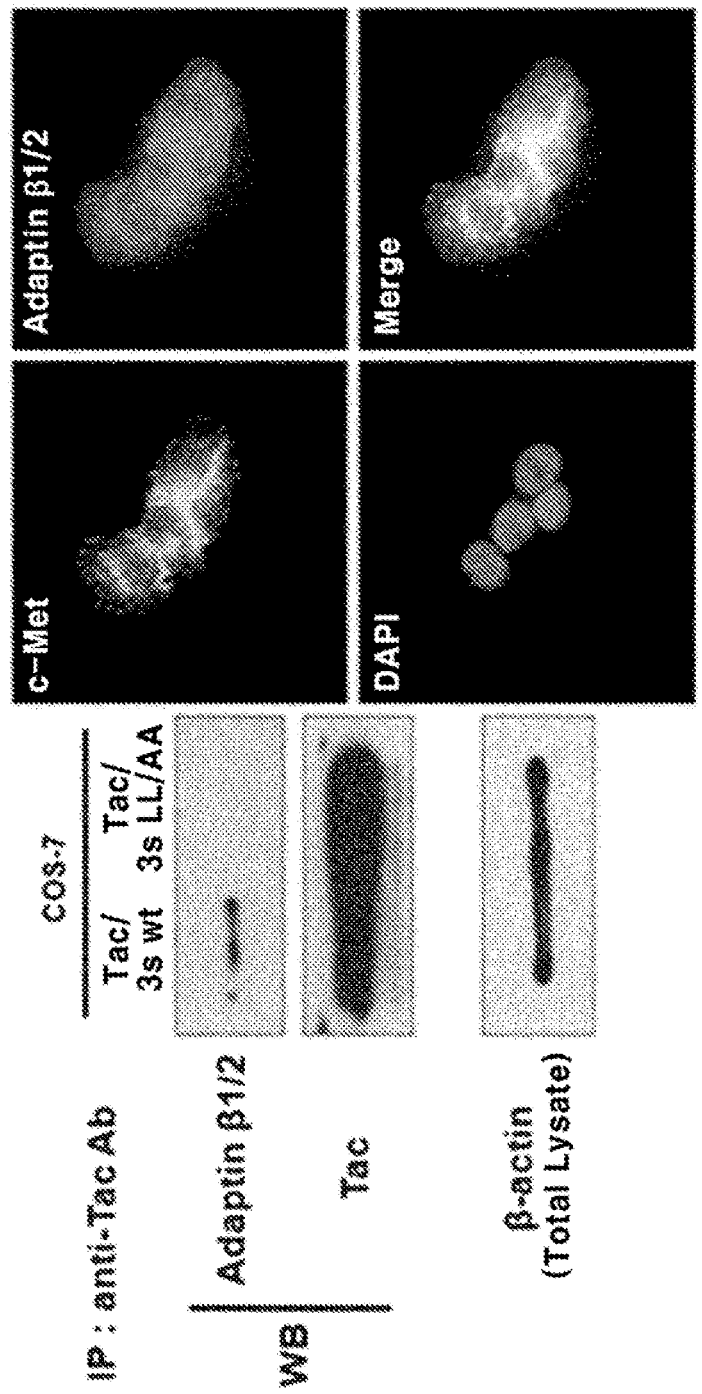
FIG. 7 is an image (left) of the result of a co-immunoprecipitation experiment showing that dileucine of c-Met is essential for interaction with β-adaptin, and a fluorescence microscopic image (right) showing colocalization of c-Met and β-adaptin in HeLa cells.

As a result, interaction of Tac/3S protein with $\beta$-adaptin was observed, but binding was interrupted when mutated motif (Tac/3SLL/AA) was replaced by dialanine, which was confirmed by fluorescence microscopy of colocalization of c-Met with $\beta$-adaptin in HeLa cells (FIG. 7). These results suggest that dileucine in the cytoplasmic tail of c-Met is crucial for the interaction of c-Met with $\beta$-adaptin.

3-4. Measurement of Internalization of Ant-3S-FITC Fusion Polypeptide in Cells

As shown in FIG. 8, in order to examine whether Ant-3S-FITC fusion polypeptide composed of Antennapedia-derived protein transduction domain (PTD, SEQ ID NO. 4) composed of 16 amino acids, endocytic motif of c-Met (3S polypeptide), and FITC (Fluorescein isothiocyanate) is easily internalized in cells, HeLa cells were treated with the polypeptide over time in the same manner as in Example 2-1, and fluorescence intensity was measured by FACS, and shown in FIG. 8. As shown in FIG. 8, MFI was only 101 at 0 minute, but reached 1166 at 30 minutes, and fluorescence was stably maintained until 120 minutes (FIG. 8). These results indicate rapid internalization of Ant-3S-FITC fusion polypeptide in cells.

3-5. Inhibitory Effect of Ant-3S-FITC Fusion Polypeptide on c-Met Endocytosis

In general, endocytosis is inhibited at 4° C. with receptors located in the cell surface, and internalized again through endocytosis when the cells are placed at 37° C. (Moore et al., Science, 236(4801):558-63, 1987). In order to examine whether Ant-3S-FITC fusion polypeptide inhibits temperature-dependent endocytosis of c-Met, HeLa cells were pretreated with Ant-3S-FITC fusion polypeptide in the same manner as in Examples 2-1 and 2-2, allowing c-Met to be endocytosed in a temperature-dependent manner. Then, FACS and fluorescence microscopy were performed to examine cell surface c-Met, and the results are shown in FIGS. 9a and 9b.

The FACS results of FIG. 9a showed that the cell surface c-Met was internalized by treatment of vehicle as temperature was increased from 4° C. to 37° C., but c-Met still remained on cell surface by treatment of Ant-3S-FITC fusion polypeptide at 37° C. The results of fluorescence microscopy also showed that c-Met endocytosis was blocked by Ant-3S-FITC fusion polypeptide, and thus c-Met remained on cell surface (FIG. 9b).

3-6. Inhibitory Effect of Ant-3S-FITC Fusion Polypeptide on HGF-dependent Endocytosis of Phospho-c-Met Binding of the c-Met ligand HGF to c-Met is known to cause c-Met endocytosis (Kamei et al., Oncogene, 18(48): 6776-84, 1999). Therefore, in order to examine whether Ant-3S-FITC fusion polypeptide inhibits HGF-dependent internalization of c-Met, HeLa and Hep3B cells were treated with Ant-3S-FITC fusion polypeptide and HGF in the same manner as in Example 2-2 so as to observe regulation of cellular distribution of phospho-c-Met (p-Met) under a fluorescence microscope, and the results are shown in FIGS. 10a and 10b.

First, when HeLa cells were treated with a low concentration of Ant-3S-FITC fusion polypeptide, a large amount of Ant-3S-FITC fusion polypeptide or a relatively small amount thereof was absorbed by some cells. Distribution of p-Met in the form of puncta was observed around the nuclei of the cells that absorbed a small amount of Ant-3S-FITC fusion polypeptide, whereas relatively uniform distribution of p-Met was observed in the cells that absorbed a large amount of Ant-3S-FITC fusion polypeptide.

To more clarify this fact, Hep3B cell line was treated with Ant-3S-FITC fusion polypeptide at various concentrations and then p-Met localization was examined. As a result, all p-Met was observed in the form of puncta in the endoplasmic reticulum. However, in the presence of high concentration of Ant-3S-FITC fusion polypeptide, no puncta was observed and p-Met was distributed throughout the cells. These results indicate that Ant-3S-FITC fusion polypeptide is able to inhibit endocytosis of phospho-c-Met as the active form (FIGS. 10a and 10b).

3-7. Inhibitory Effect of Ant-3S-FITC Fusion Polypeptide on Autophosphorylation of c-Met Binding of the c-Met ligand, HGF to c-Met induces autophosphorylation of c-Met and the activation of various proteins (Comoglio et al., EXS, 65:131-65, 1993). Therefore, in order to examine how Ant-3S-FITC fusion polypeptide regulates HGF-induced autophosphorylation of c-Met and downstream signaling. Western blotting was performed in the same manner as in Example 2-3, and the results are shown in FIG. 11.

Figure 12:
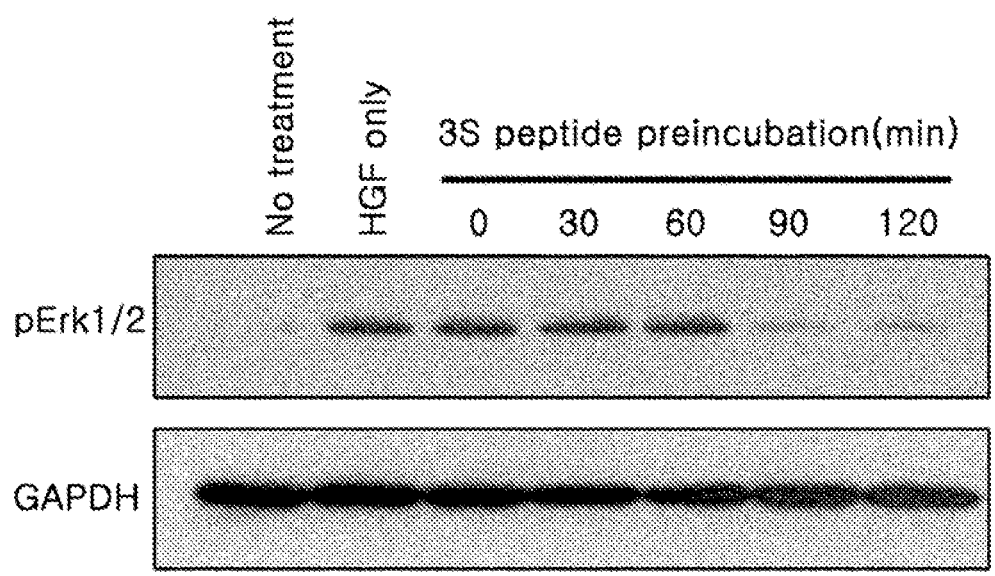
FIG. 12 is a Western blot image showing that Ant-3S-FITC fusion polypeptide can inhibit HGF-induced autophosphorylation of Erk1/2 after preincubation for 90 minutes.
Figure 13:
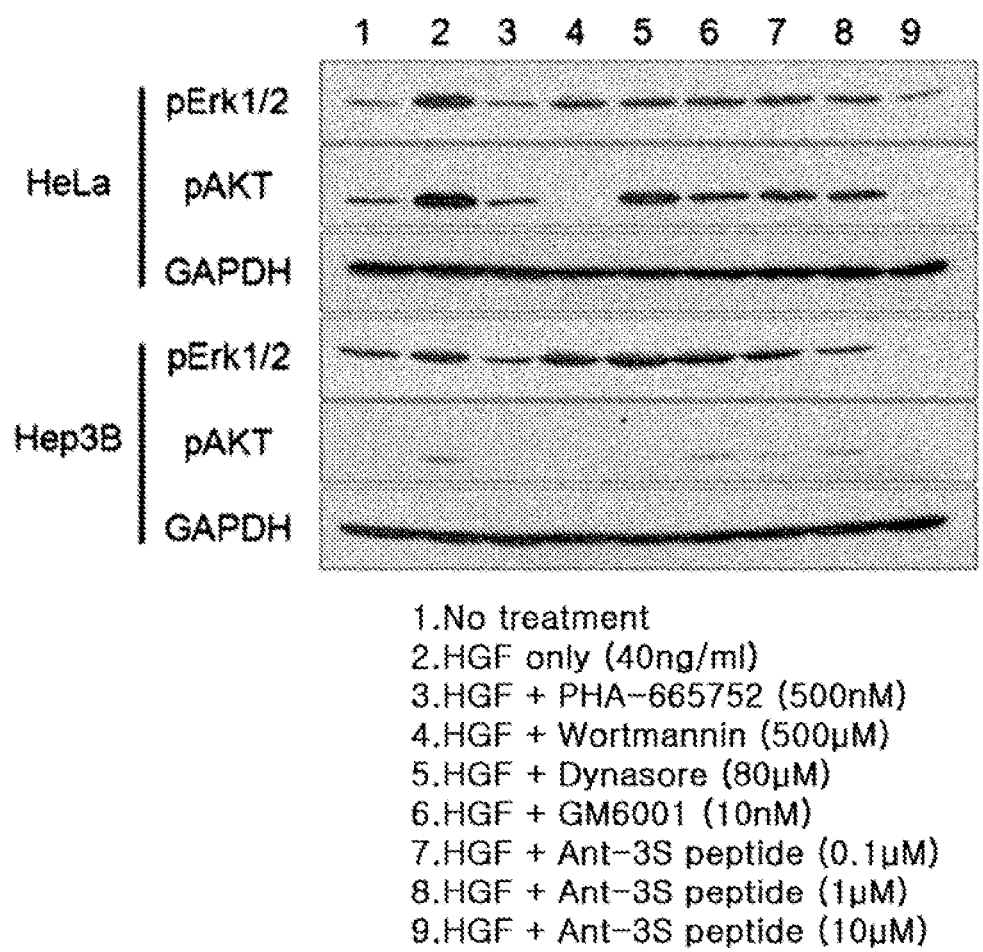
FIG. 13 is a Western blot image showing that Ant-3S-FITC fusion polypeptide can inhibit HGF-induced autophosphorylation of Erk1/2 and AKT, compared to other inhibitors.

As shown in FIG. 11, as the treatment concentration of Ant-3S-FITC fusion polypeptide increased, autophosphorylation of c-Met was inhibited. Phosphorylation of FAK was decreased in a dose-dependent manner (FIG. 11). Further, phosphorylation of AKT and Erk1/2 was also inhibited by Ant-3S-FITC fusion polypeptide (FIGS. 12 and 13).

3-8. Inhibitory Effect of Ant-3S-FITC Fusion Polypeptide on HGF-dependant Migration In order to examine whether HGF-dependent migration is inhibited by Ant-3S-FITC fusion polypeptide, MTT assay was performed in the same manner as in Example 2-6, and the results are shown in FIG. 14.

As shown in FIG. 14, as the concentration of Ant-3S-FITC fusion polypeptide increased, proliferation of Hep3B cell line was inhibited (FIG. 14). Furthermore, the results of the TRANSWELL migration assay as in Example 2-5 and the MDCK scattering assay as in Example 2-8 showed that Ant-3S-FITC fusion polypeptide is able to inhibit HGF-dependent migration of Hep3B and MDCK cells (FIGS. 15, 16a and 16b).

These results suggest that Ant-3S-FITC fusion polypeptide can be used as a therapeutic agent for inhibiting metastasis of cancer cells.

3-9. Inhibitory Effect of Ant-3S-FITC Fusion Polypeptide on c-Met Specific Endocytosis In order to examine whether Ant-3S-FITC fusion polypeptide including PSLL sequence can inhibit endocytosis of GLUT4 including PSLL sequence, or inhibit only c-Met endocytosis, and furthermore, whether it affects endocytosis of other receptors including no PSLL sequence, Tac/3S and Tac/PSD95 chimeric proteins, and GLUT4-HA protein tagged with HA were expressed in COS-7 cell line, and temperature-dependent endocytosis by 3S-FITC fusion polypeptide was examined by fluorescence microscopy, and the results are shown in FIG. 17.

Figure 17:
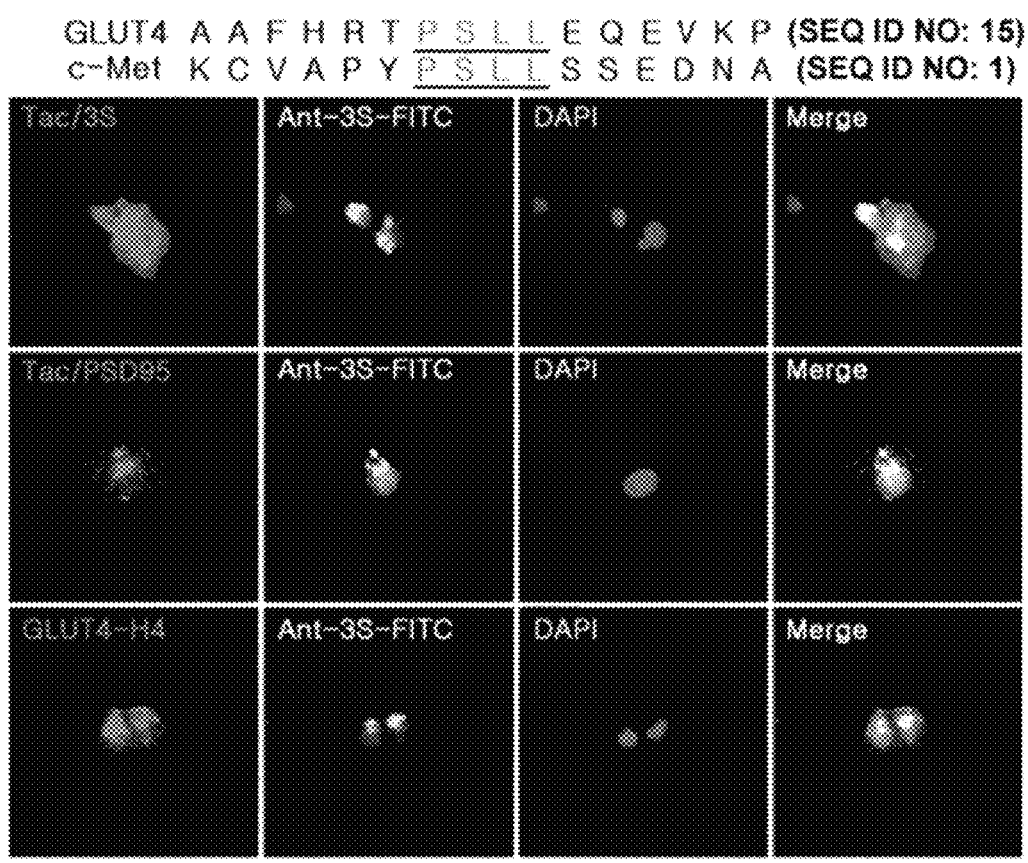
FIG. 17 is fluorescence microscopic images showing that Ant-3S-FITC fusion polypeptide does not affect endocytosis of receptors other than c-Met.

As shown in FIG. 17, Ant-3S-FITC fusion polypeptide effectively inhibited endocytosis of Tac/3S chimeric protein, but did not affect endocytosis of Tac/PSD95 and GLUT4-HA proteins (FIG. 17). These results indicate that Ant-3S-FITC fusion polypeptide specifically inhibits c-Met endocytosis.

It will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within the metes and bounds of the claims, or the equivalents of such metes and bounds are therefore intended to be embraced by the claims.

What is claimed is:

1. A method for treating cancer, comprising administering a fusion polypeptide to a subject having cancer or being at risk of having cancer, wherein the fusion polypeptide is represented by the amino acid sequence of SEQ ID NO: 10, wherein the cancer is one or more selected from the group consisting of hepatocellular carcinoma and cervical cancer.

2. The method according to claim 1, wherein the treatment is performed by inhibiting metastasis or growth of cancer.

3. The method according to claim 1, wherein the fusion polypeptide inhibits endocytosis of one or more selected from the group consisting of c-Met, phosphorylated c-Met and c-Met bound to hepatocyte growth factor (HGF).

4. The method according to claim 1, wherein the fusion polypeptide inhibits hepatocyte growth factor (HGF)-induced autophosphorylation of c-Met.

5. A method for inhibiting metastasis of cancer, comprising administering a fusion polypeptide to a subject having cancer, wherein the fusion polypeptide is represented by the amino acid sequence of SEQ ID NO: 10, wherein the cancer is one or more selected from the group consisting of hepatocellular carcinoma and cervical cancer.

6. A method for inhibiting endocytosis of one or more selected from the group consisting of c-Met, phosphorylated c-Met and c-Met bound to hepatocyte growth factor (HGF), comprising administering a fusion polypeptide to a subject, wherein the fusion polypeptide is represented by the amino acid sequence of SEQ ID NO: 10.

* * * * *

SEQUENCE LISTING

<160> NUMBER OF SEQ ID NOS: 10

<210> SEQ ID NO 1
<211> LENGTH: 16
<212> TYPE: PRT
<213> ORGANISM: Artificial Sequence
<220> FEATURE:
<223> OTHER INFORMATION: endocytic motif(3S)

<400> SEQUENCE: 1

-continued

```
Lys Cys Val Ala Pro Tyr Pro Ser Leu Leu Ser Ser Glu Asp Asn Ala
  1               5                  10                  15

<210> SEQ ID NO 2
<211> LENGTH: 11
<212> TYPE: PRT
<213> ORGANISM: Artificial Sequence
<220> FEATURE:
<223> OTHER INFORMATION: Tat of HIV(human immunodeficiency virus)

<400> SEQUENCE: 2

Tyr Gly Arg Lys Lys Arg Arg Gln Arg Arg Arg
  1               5                  10

<210> SEQ ID NO 3
<211> LENGTH: 34
<212> TYPE: PRT
<213> ORGANISM: Artificial Sequence
<220> FEATURE:
<223> OTHER INFORMATION: VP22 of HSV(Herpes simplex virus)

<400> SEQUENCE: 3

Asp Ala Ala Thr Ala Thr Arg Gly Arg Ser Ala Ala Ser Arg Pro Thr
  1               5                  10                  15

Glu Arg Pro Arg Ala Pro Ala Arg Ser Ala Ser Ala Pro Arg Arg Pro
             20                  25                  30

Val Glu

<210> SEQ ID NO 4
<211> LENGTH: 16
<212> TYPE: PRT
<213> ORGANISM: Artificial Sequence
<220> FEATURE:
<223> OTHER INFORMATION: antennapedia of Drosophila

<400> SEQUENCE: 4

Arg Gln Ile Lys Ile Trp Phe Gln Asn Arg Arg Met Lys Trp Lys Lys
  1               5                  10                  15

<210> SEQ ID NO 5
<211> LENGTH: 11
<212> TYPE: PRT
<213> ORGANISM: Artificial Sequence
<220> FEATURE:
<223> OTHER INFORMATION: Protein transduction domain Mph-1

<400> SEQUENCE: 5

Tyr Ala Arg Val Arg Arg Arg Gly Pro Arg Arg
  1               5                  10

<210> SEQ ID NO 6
<211> LENGTH: 9
<212> TYPE: PRT
<213> ORGANISM: Artificial Sequence
<220> FEATURE:
<223> OTHER INFORMATION: Protein transduction domain Sim-2

<400> SEQUENCE: 6

Ala Lys Ala Ala Arg Gln Ala Ala Arg
  1               5

<210> SEQ ID NO 7
<211> LENGTH: 7
<212> TYPE: PRT
<213> ORGANISM: Artificial Sequence
```

```
<220> FEATURE:
<223> OTHER INFORMATION: Protein transduction domain R7

<400> SEQUENCE: 7

Arg Arg Arg Arg Arg Arg Arg
 1               5

<210> SEQ ID NO 8
<211> LENGTH: 21
<212> TYPE: PRT
<213> ORGANISM: Artificial Sequence
<220> FEATURE:
<223> OTHER INFORMATION: Protein transduction domain Pep-1

<400> SEQUENCE: 8

Leu Glu Thr Trp Trp Glu Thr Trp Trp Thr Glu Trp Ser Gln Pro Lys
 1               5                  10                  15

Lys Lys Arg Lys Val
            20

<210> SEQ ID NO 9
<211> LENGTH: 21
<212> TYPE: PRT
<213> ORGANISM: Artificial Sequence
<220> FEATURE:
<223> OTHER INFORMATION: Protein transduction domain Pep-2

<400> SEQUENCE: 9

Lys Glu Thr Trp Phe Glu Thr Trp Phe Thr Glu Trp Ser Gln Pro Lys
 1               5                  10                  15

Lys Lys Arg Lys Val
            20

<210> SEQ ID NO 10
<211> LENGTH: 32
<212> TYPE: PRT
<213> ORGANISM: Artificial Sequence
<220> FEATURE:
<223> OTHER INFORMATION: Antp-endocytic motif fusion polypeptide

<400> SEQUENCE: 10

Arg Gln Ile Lys Ile Trp Phe Gln Asn Arg Arg Met Lys Trp Lys Lys
 1               5                  10                  15

Lys Cys Val Ala Pro Tyr Pro Ser Leu Leu Ser Ser Glu Asp Asn Ala
            20                  25                  30
```